United States Patent
Ezrielev et al.

(10) Patent No.: US 12,249,070 B2
(45) Date of Patent: Mar. 11, 2025

(54) SYSTEM AND METHOD FOR IMAGE EXPLORATION USING AREAS OF INTEREST

(71) Applicant: Dell Products L.P., Round Rock, TX (US)

(72) Inventors: Ofir Ezrielev, Be'er Sheva (IL); Amihai Savir, Newton, MA (US); Avitan Gefen, Lehavim (IL); Nicole Reineke, Northborough, MA (US)

(73) Assignee: Dell Products L.P., Round Rock, TX (US)

( * ) Notice: Subject to any disclaimer, the term of this patent is extended or adjusted under 35 U.S.C. 154(b) by 374 days.

(21) Appl. No.: 17/872,944

(22) Filed: Jul. 25, 2022

(65) Prior Publication Data
US 2024/0029242 A1    Jan. 25, 2024

(51) Int. Cl.
G06K 9/00   (2022.01)
G06F 12/0811   (2016.01)
G06T 7/00   (2017.01)
G06T 7/11   (2017.01)
G16H 30/40   (2018.01)

(52) U.S. Cl.
CPC ........ *G06T 7/0012* (2013.01); *G06F 12/0811* (2013.01); *G06T 7/11* (2017.01); *G16H 30/40* (2018.01); *G06T 2207/20104* (2013.01)

(58) Field of Classification Search
CPC .................................................. G06F 12/0811
See application file for complete search history.

(56) References Cited

U.S. PATENT DOCUMENTS

| 6,246,804 | B1 | 6/2001 | Sato et al. | |
| 8,576,238 | B1* | 11/2013 | Brandt | G06T 15/005 |
| | | | | 345/428 |
| 8,862,741 | B1* | 10/2014 | Tegtmeier | H04L 67/10 |
| | | | | 709/226 |
| 8,873,836 | B1 | 10/2014 | Dietrich | |
| 8,935,474 | B1* | 1/2015 | Todd | G06F 12/08 |
| | | | | 711/117 |
| 9,665,799 | B1* | 5/2017 | Munteanu | G06V 10/955 |

(Continued)

FOREIGN PATENT DOCUMENTS

| WO | 2008/012717 A2 | 1/2008 |
| WO | 2022/064409 A1 | 3/2022 |

OTHER PUBLICATIONS

Goodfellow, Ian J., et al. "Generative Adversarial Nets", Departement d'informatique et de recherche operationnelle, Universite de Montreal, Montreal, QC H3C 3J7, Canada. arXiv:1406.2661v1 [stat.ML] Jun. 10, 2014. 9 pages.

(Continued)

*Primary Examiner* — Hadi Akhavannik
(74) *Attorney, Agent, or Firm* — Womble Bond Dickinson (US) LLP / (EMC IP Holding)

(57) ABSTRACT

Methods and systems for identifying areas of interest in an image and management of images are disclosed. To manage identification of areas of interest in an image, subject matter expert driven processes may be used to identify the areas of interest. The identified areas of interest may be used to establish plans to guide subsequent use of the image. The identified areas of interest may also be used to establish plans to cache portions of the image to speed subsequent use of the image.

20 Claims, 12 Drawing Sheets

(56) References Cited

U.S. PATENT DOCUMENTS

| | | | |
|---|---|---|---|
| 10,109,051 B1 | 10/2018 | Natesh et al. | |
| 2001/0030667 A1* | 10/2001 | Kelts | G06F 16/444 |
| | | | 715/854 |
| 2004/0117358 A1* | 6/2004 | von Kaenel | G06Q 40/08 |
| 2007/0064981 A1 | 3/2007 | Meijer | |
| 2008/0184068 A1* | 7/2008 | Mogi | G06F 11/1469 |
| | | | 714/15 |
| 2009/0074275 A1 | 3/2009 | O Ruanaidh | |
| 2009/0210427 A1 | 8/2009 | Eidler | |
| 2011/0110568 A1* | 5/2011 | Vesper | G06Q 10/10 |
| | | | 382/128 |
| 2013/0162664 A1* | 6/2013 | Peacock | G06T 1/60 |
| | | | 345/543 |
| 2014/0002466 A1 | 1/2014 | Paragios | |
| 2015/0073909 A1* | 3/2015 | Peden | G06Q 30/0267 |
| | | | 705/14.58 |
| 2015/0134661 A1* | 5/2015 | Circlaeys | G06F 16/438 |
| | | | 707/752 |
| 2015/0278249 A1 | 10/2015 | Akiyama et al. | |
| 2015/0332111 A1 | 11/2015 | Kisilev | |
| 2016/0062689 A1* | 3/2016 | Cherubini | G06F 3/0608 |
| | | | 711/159 |
| 2019/0011703 A1 | 1/2019 | Robaina | |
| 2020/0092571 A1 | 3/2020 | Tourapis | |
| 2020/0234451 A1 | 7/2020 | Holzer | |
| 2020/0285880 A1 | 9/2020 | Sedai | |
| 2020/0372718 A1* | 11/2020 | Molyneaux | H04N 13/239 |
| 2020/0411164 A1 | 12/2020 | Donner | |
| 2021/0073449 A1 | 3/2021 | Segev | |
| 2021/0150682 A1 | 5/2021 | Sytnik | |
| 2021/0209488 A1 | 7/2021 | Li | |
| 2021/0233213 A1 | 7/2021 | Mejjati | |
| 2021/0383242 A1 | 12/2021 | Ostyakov | |
| 2022/0076411 A1 | 3/2022 | Georgescu | |
| 2022/0116549 A1 | 4/2022 | Neofytou | |
| 2022/0284118 A1 | 9/2022 | Kaul | |
| 2023/0206447 A1 | 6/2023 | Kobayashi et al. | |

OTHER PUBLICATIONS

Radford, Alec, et al. "Unsupervised Representation Learning with Deep Convolutional Generative Adversarial Networks", indico Research, Boston, MA. Under review as a conference paper at ICLR 2016. arXiv:1511.06434v2 [cs.LG] Jan. 7, 2016. 16 pages.

Goodfellow, Ian, "NIPS 2016 Tutorial: Generative Adversarial Networks", OpenAI. arXiv:1701.00160v4 [cs.LG] Apr. 3, 2017. 57 pages.

Allwardt, Vanessa, et al. "Translational Roadmap for the Organs-on-a-Chip Industry toward Broad Adoption", Bioengineering 2020, 7, 112; Sep. 16, 2020. 27 pages.

Kilic, Tugba, et al. "Organs-on-chip monitoring: sensors and other strategies", Microphysiological Systems, 2018; 2:5; Sep. 5, 2018. 32 pages.

"Causal Discovery from Spatio-Temporal Data with Applications to Climate Science", Ebert-Uphoff, Imme, School of Electrical and Computer Engineering, Colorado State University, Fort Collins, CO; and Deng, Yi, School of Earth and Atmospheric Sciences, Georgia Institute of Technology, Atlanta, GA. Dec. 2014. 8 pages.

Microscopy Software, "Your Complete Solution from Sample to Knowledge", Zeiss; Carl Zeiss Microscopy GmbH, 07745 Jena, Germany. Jul. 2021. 28 pages.

Zen Data Storage and Data Explorer, "Smart data management in life sciences", Zeiss; updated: Oct. 2020; Carl Zeiss Microscopy GmbH, 07745 Jena, Germany; Oct. 2020. 4 pages.

Torfi, Amirsina, et al. "Differentially Private Synthetic Medical Data Generation using Convolutional GANs", ARXIV Submission Version. arXiv:2012.11774v1 [cs.LG] Dec. 22, 2020. 13 pages.

Lena Oden, "Comparing Data Staging Techniques for Large Scale Brain Images", IEEE Transactions on Emerging Topics in Computing, Dec. 6, 2021, 12 pages (Year: 2021).

\* cited by examiner

SYSTEM AND METHOD FOR IMAGE EXPLORATION USING AREAS OF INTEREST

FIELD

Embodiments disclosed herein relate generally to image classification. More particularly, embodiments disclosed herein relate to systems and methods to manage the classification of areas of interest in an image.

BACKGROUND

Computing devices may provide computer-implemented services. The computer-implemented services may be used by users of the computing devices and/or devices operably connected to the computing devices. The computer-implemented services may be performed with hardware components such as processors, memory modules, storage devices, and communication devices. The operation of these components and the components of other devices may impact the performance of the computer-implemented services.

BRIEF DESCRIPTION OF THE DRAWINGS

Embodiments disclosed herein are illustrated by way of example and not limitation in the figures of the accompanying drawings in which like references indicate similar elements.

DETAILED DESCRIPTION

Figure 1:
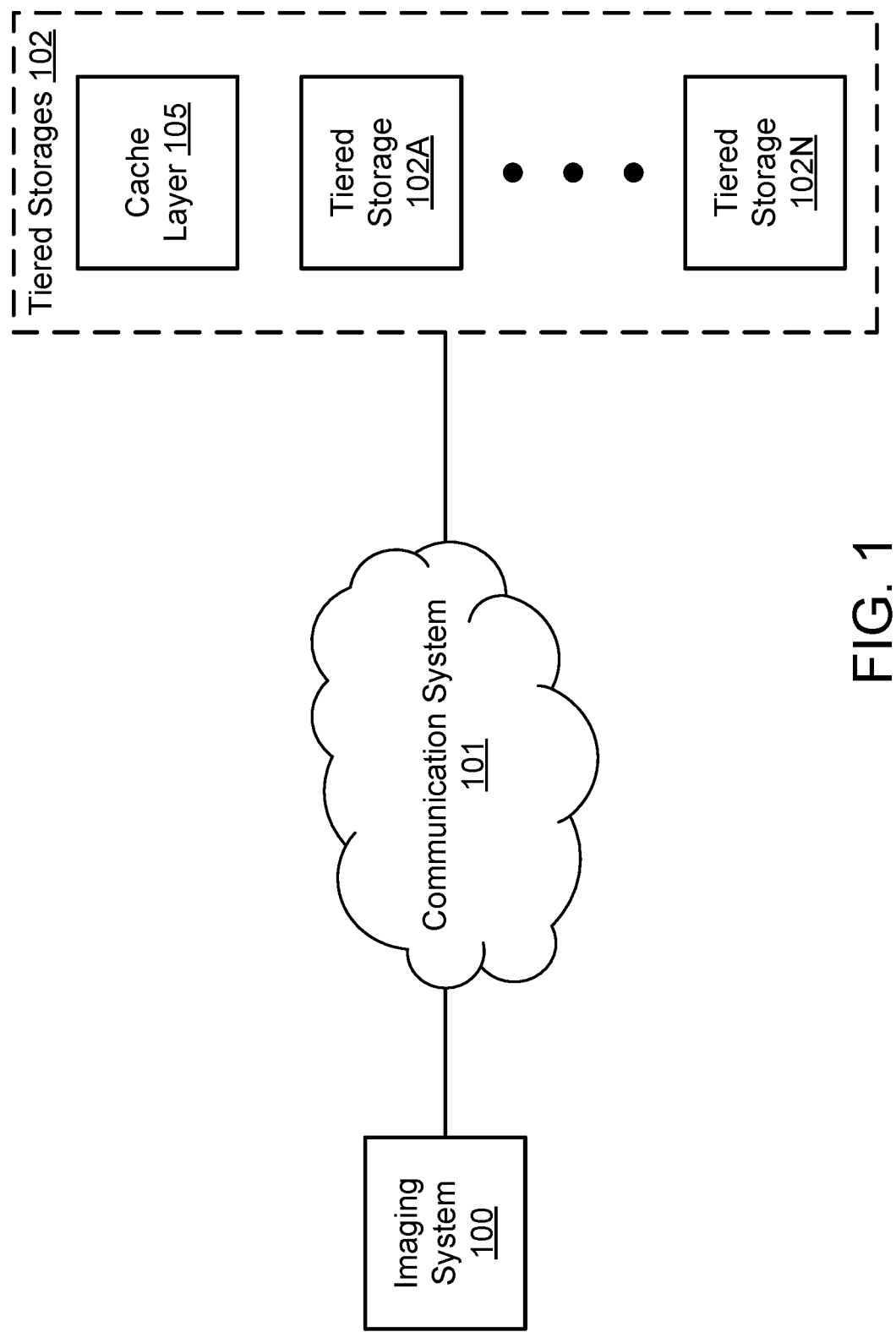
FIG. 1 shows a block diagram illustrating a system in accordance with an embodiment.

Various embodiments will be described with reference to details discussed below, and the accompanying drawings will illustrate the various embodiments. The following description and drawings are illustrative and are not to be construed as limiting. Numerous specific details are described to provide a thorough understanding of various embodiments. However, in certain instances, well-known or conventional details are not described in order to provide a concise discussion of embodiments disclosed herein.

Reference in the specification to "one embodiment" or "an embodiment" means that a particular feature, structure, or characteristic described in conjunction with the embodiment can be included in at least one embodiment. The appearances of the phrases "in one embodiment" and "an embodiment" in various places in the specification do not necessarily all refer to the same embodiment.

In general, embodiments disclosed herein relate to methods and systems for identifying areas of interest in an image and using the identified areas of interest to manage subsequent use of the image. To identify areas of interest in an image, the system may include an imaging system. The imaging system may cooperate with a subject matter expert to identify areas of interest in an image. Various processes and/or services may be keyed to the areas of interest, and the areas of interest may be provided to a downstream consumer in order to facilitate further analysis and/or interpretation of the image. For example, areas of interest may be relevant in medical settings to diagnose medical conditions.

Once identified, the areas of interest may be used to manage storage of the image across varying tiers of storage to manage cost and performance, to manage caching of various portions of the image to improve read time during subsequent use of the image, and/or to guide subsequent use of the image. To guide subsequent use of the image, ordering between the areas of interest may be used to direct the attention of a user of the image. For example, graphical elements may be instantiated that direct a user's attention to areas of interest in a predetermined order. The order may correspond, for example, to the same order in which the areas of interest were identified by the subject matter expert.

By doing so, subsequent users of the image may be provided with additional information regarding previous uses of the image. In a medical context where time may be of great importance, the additional information may reduce a time to either confirm or reject a previously made diagnosis.

Additionally, when areas of interest are identified, the areas of interest may be classified based on a role of the subject matter expert identifying the areas of interest. Consequently, when multiple subject matter experts identify areas of interest, only those areas of interest relevant to a particular downstream consumer may be utilized when the image is subsequently used. In the medical context, for example, many medical professionals with a wide range of different expertise may identify areas of interest that are relevant for certain purposes and irrelevant for others. The subsequent uses of the images may be guided based only on those annotations relevant to the person use the image. For example, a title, role, or other characteristic of previous and subsequent users may be used to identify relevant areas of interest.

By doing so, embodiments disclosed herein may provide a system that identifies both areas of interest in an image and uses the areas of interest to manage subsequent use.

In an embodiment, a method for managing exploration of an image that is segmented into image segments which are stored across storage tiers is provided. The method may include identifying initiation of an interpretation of the image; identifying areas of interest in the image; during the interpretation of the image: dynamically updating a cached portion of the image segments in a cache layer based on: the areas of interest, and a current view of the image presented to an interpreter of the image; generating, responsive to input from the interpreter of the image, frames for display on a display using the cached portion of the image segments from the cache layer to facilitate the interpretation of the image.

Dynamically updating the cached portion of the image segments may include, for an update of the cached portion: identifying an area of interest of the areas of interest that is depicted in the current view; identifying a second area of interest of the area of interest that is not in the current view but is associated with the area of interest based on a previous interpretation of the image; and adding a portion of the image segments of the image that correspond to the second area of interest to the cached portion of the image segments in the cache layer.

Dynamically updating the cached portion of the image segments further may include, for the update of the cached portion: adding a second portion of the image segments of the image that correspond to a path between the area of interest and the second area of interest to the cached portion of the image segments in the cache layer.

Dynamically updating the cached portion of the image segments may also include, for the update of the cached portion: adding a third portion of the image segments of the image that correspond to a periphery around the current view to the cached portion of the image segments in the cache layer.

The areas of interest may correspond to portions of the image annotated during a previous interpretation of the image.

The areas of interest may be associated with one another based on distances between pairs of the areas of interest.

Generating, responsive to the input from the interpreter of the image, the frames may include, for a frame of the frame: adding a representation of a navigation tool to the frame, the navigation tool indicating transitioning the current view from depicting the area of interest to a second area of interest of the areas of interest. Generating, responsive to the input from the interpreter of the image, the frames may also include, for the frame of the frame: using a portion of the cached portion of the image segments in the cache layer to generate a representation of the image for the current view.

A non-transitory media may include instructions that when executed by a processor cause the computer-implemented method to be performed.

A data processing system may include the non-transitory media and a processor, and may perform the computer-implemented method when the computer instructions are executed by the processor.

Turning to FIG. 1, a block diagram illustrating a system in accordance with an embodiment is shown. The system shown in FIG. 1 may provide computer-implemented services that may utilize images as part of the provided computer-implemented services.

The images may include, for example, super resolution images or other types of images of large size (and/or other sizes). The images may depict various types of scenes which may be useful for a range of purposes. For example, the images may depict scenes useful for medical diagnosis, accident analysis, surveying, and/or other types of purposes.

The computer-implemented services may include any type and quantity of computer-implemented services. The computer-implemented services may include, for example, (i) analysis services through which the images may be analyzed and information derived from the images may be obtained, (ii) data storage services for storing and providing copies of the images over time, and/or (iii) any other type of computer-implemented services that may be performed, at least in part, using images (e.g., image files).

To facilitate use of the images as part of the computer-implemented services, areas of interest in an image may be obtained and stored for future use. These areas of interest may be relevant to a use of the image.

For example, a subject matter expert (SME) may be a medical professional that is tasked with reviewing and making a medical diagnosis based on the image. As part of the diagnostic process performed by the SME, the SME may review various portions of the image and annotate areas of interest that are highly diagnostically relevant to the medical diagnosis. These areas of interest may be used during subsequent uses of the image. For example, a second SME is tasked with reviewing the medical diagnosis, the second SME may use the areas of interest to guide subsequent review of the image. The areas of interest may highlight landmarks or other key portions of the scene depicted in the image that drove the previously made medical diagnosis.

In general, embodiments disclosed herein may provide methods, systems, and/or devices for managing images based on areas of interest in the images. To manage the images based on the areas of interest, the areas of interest may be used to (i) drive caching behavior expedite loading and use of the image during uses of the image, (ii) guide subsequent use of the image by directing a subsequent user to the portions of the image associated with the areas of interest, and/or (iii) storage of the image, or portions thereof, to manage both cost and storage performance. By doing so, embodiments disclosed herein may provide a system capable of managing images to decrease storage cost, improve performance of processes that use the image, and/or expedite use by directing attention of SMEs (and/or automated systems) to portions of the image that are more likely to be relevant than other portions that are less likely to be relevant for subsequent uses.

To obtain and process images, the system of FIG. 1 may include imaging system 100. Imaging system 100 may obtain images, identify areas of interest in the image, store the images (and/or portions thereof) in storages (e.g., tiered storages 102) based on the likelihood of future access of each image and/or portions thereof, cache the images based on the area of interest during subsequent use, and guide use of the images based on the areas of interest.

The areas of interest may be identified through computer automation and/or in cooperation with one or more SMEs. For example, images (or portions thereof) may be presented to the SMEs as part of an interpretation process so that the SMEs may explore the images and identify areas of interest based on their expertise. The areas of interest may be sub-portions of the images (e.g., some number of pixels of the images). While illustrated in subsequent figures as rectangular areas, areas of interest (primary and/or auxiliary) may be of any shape without departing from embodiments disclosed herein. Any of the areas of interest may include, for example, one or more landmarks. A landmark may be a portion of a scene depicted in an image that is relevant to an outcome with respect to a use of an image. In a medical context, a landmark may be a collection of cells, a portion of tissue, and/or other features of a depicted scene that the SME is trained to identify and/or use in making a medical diagnosis.

To manage the areas of interest, areas of interest may be classified based on a role of the SME that added the area of interest. These classifications may be used to filter areas of interest that are unlikely to be useful to certain subsequent users.

While described with respect to medical diagnosis above, it will be appreciated that the areas of interest identified through automated and/or cooperative approaches may be used to achieve other types of goals.

Areas of interest (e.g., primary and/or auxiliary) may be provided (and/or identified) to a downstream consumer along with or separate from the image and/or outcome of a process for which the image is used as part of the computer-implemented services provided by the system. In an embodiment, the computer-implemented services may include storing the areas of interest (and/or corresponding image segments or images) in storage tiers of varying performance levels. In order to manage the storage of areas of interest and/or a corresponding image, (i) the image may be segmented, (ii) the image segments may be classified based on the areas of interest (e.g., based on each image segments membership in various areas of interest), (iii) the image segment may be allocated for different storage tiers depending on the likelihood of future access of each image segment, (iv) the image segments may be stored in storages of varying storage tiers based on the allocation for each respective image segment so that image segments that are more likely to be accessed in the future are stored in higher performance storage tiers and image segments that are less likely to be accessed in the future are stored in lower performance storage tiers, and/or (v) plans for managing caching and/or use of the image during subsequent uses may be stored (e.g., with the image in the storage tier and/or in other locations). By doing so, embodiments disclosed herein may provide a more responsive system by improving the efficiency of resource allocation for accessing images while limiting cost incurred for responsiveness of the system.

For example, if an image segment includes a portion of the image that is within an area of interest, the image segment may be treated as having a high likelihood (or another level of likelihood depending on the level of area of interest in a hierarchy) of being accessed in the future. In another example, if an image segment is not within any areas of interest, the image segment may be treated as having a low likelihood of being accessed in the future. In a still further example, if an image segment is partially within an area of interest (e.g., straddles a boundary of an area of interest), then the image segment may be treated as having a medium likelihood of being accessed in the future. Other criteria may be used to ascertain the level of likelihood of an image segment being accessed in the future may be used without departing from embodiments disclosed herein. For example, image segments within auxiliary areas of interest designated as being diagnostically irrelevant may be stored in archival storage tiers or allocated for extremely cost effective storage tiers.

In addition to area of interest membership, the likelihood of an image segment being accessed in the future may also take into account a type of an area of interest. For example, when an image is processed different types of areas of interest may be identified (e.g., primary and auxiliary areas of interest). The types of the area of interest may define a hierarchy with respect to the areas of interest. The hierarchy may define a level of relevancy of each type of area of interest with respect to a purpose (e.g., a medical diagnosis) for which the image is annotated with the areas of interest.

For example, if an image segment is within an area of interest that is at a top of the hierarchy (e.g., a primary area of interest), the image segment may be treated as having a high likelihood of being accessed in the future. In a second example, if an image segment is within an area of interest that is in the middle of the hierarchy (e.g., an auxiliary area of interest designated as diagnostically relevant), the image segment may be treated as having a high (or medium) likelihood of being accessed in the future. In a third example, if an image segment is within an area of interest that is at a bottom of the hierarchy (e.g., an auxiliary area of interest designated as diagnostically irrelevant), the image segment may be treated as having a low likelihood of being accessed in the future.

To allocate the image segments for storage, imaging system 100 may perform a lookup to identify a storage plan or may otherwise identify a storage plan (e.g., based on an association) for an image segment based on the likelihood of the image segment being accessed in the future. The storage plan may specify (i) a storage tier, (ii) a migration plan between storage tiers (e.g., transferring image segments between tiered storages at different points in time), (iii) a fidelity level (e.g., resolution) for an image segment, and/or (iv) other information that defines how an image segment will be stored for future use. The storage plan may define the allocation for the image segment.

Once allocated, imaging system 100 may store the image segments in corresponding tiered storages of tiered storages 102. Tiered storages 102 may store image segments and/or other data structures. Tiered storages 102 may include any number of tiered storages (e.g., 102A, 102N). Different tiered storages may provide different quality levels with respect to storing data and/or providing copies of stored data. For example, different tiered storages may be implemented with different types and/or quantities of hardware devices. Consequently, different storage tiers may be more or less costly to implement depending on hardware/software components used to implement the storage tiers. To manage cost, tiered storages 102 may include tiered storages with different levels of performance and associated cost. Accordingly, imaging system 100 may store image segments that are more likely to be accessed in the future in higher performance storage tiers (which may have higher associated costs) and other image segments that are less likely to be accessed in the future in lower performance storage tiers.

In an embodiment, tiered storages 102 is implemented with a range of different storage tiers providing different levels of performance having corresponding levels of associated cost. Thus, the image segments may be distributed to the different storage tiers based on corresponding likelihoods of future access.

In an embodiment, tiered storages 102 is implemented with two storage tiers that provide different levels of performance having corresponding levels of associated cost. The image segments associated with areas of interest may be stored in a higher performance tiered storage and the image segments not associated with areas of interest may be stored in lower performance tiered storage.

After an image is stored in tiered storages 102, the image may be read for subsequent use. For example, a subject matter expert may be tasked with reinterpreting an image. To do so, portions of the image may need to be read. However, because some image segments may be stored in low performance storage, it may not be practical to read the image segments from the low performance storage as various portions of the image are to be displayed.

To improve read performance, some of the image segments may be cached in cache layer 105. The selection of image segments cached may be dynamically updated based on the portion of the image being viewed/used. For example, a current view may include one or more areas of interest which may be linked to other areas of interest, paths between the areas of interest, and/or supplemental areas via one or more plans. These plans may be used to select image segments to add to the cache when the cache is dynamically updated.

Cache layer 105 may be implemented, for example, with higher performance storage and/or memory devices. Cache layer 105 may include, for example, controllers usable to manage cache behavior of cache layer 105. The cache behavior may be keyed to the area of interest plans for an image and portions of an image that are in use (e.g., being viewed).

Consequently, when an indication of an area of interest in an image is obtained (e.g., based on use of the image), the controller may automatically identify other areas of interest, portions of the image corresponding to paths and/or supplemental areas based on a corresponding area of interest plan, and automatically cache the image segments stored in tiered storage 102A-102N corresponding to these identified portions of the image (e.g., the specified areas of interest, paths between areas of interest, and supplemental areas such as areas around areas of interest). By doing so, portions of the image more likely to be subsequently used may be cached ahead of the use. Consequently, to service the use, it may be more likely that the necessary portions of the image segments are available in cache layer 105, thereby avoiding reads directed to lower performance tiered storages.

To customize both caching behavior and subsequent use, multiple types of cache and area of interest plans may be established. These plans may be established for each classification of area of interest. Consequently, the cache and area of interest plans may be filtered so that only those that are likely to be helpful to a subsequent user of the image may be implemented to manage the image and use of the image. For example, if two sets of areas of interest were identified by two different medical professionals, corresponding plans may be established so that when a subsequent medical professional desires to use the image in the future only those plans corresponding to a similar specialty, role, or job function may be implemented. In this manner, the behavior of the system may be customized based on the roles of the previous users and current user of an image.

When performing its functionality, one or more of imaging system 100 and tiered storages 102 may perform all, or a portion, of the methods and/or actions shown in FIGS. 3A-4E.

Any of imaging system 100 and tiered storages 102 may be implemented using a computing device (e.g., a data processing system) such as a host or a server, a personal computer (e.g., desktops, laptops, and tablets), a "thin" client, a personal digital assistant (PDA), a Web enabled appliance, a mobile phone (e.g., Smartphone), an embedded system, local controllers, an edge node, and/or any other type of data processing device or system. For additional details regarding computing devices, refer to FIG. 5.

In an embodiment, imaging system 100 is implemented using multiple computing devices. For example, an initial interpreter of an image may use a first computing device of imaging system 100 and a second, subsequent interpreter of an image may use a second computing device of imaging system 100.

Any of the components illustrated in FIG. 1 may be operably connected to each other (and/or components not illustrated) with a communication system (e.g., 101).

In an embodiment, communication system 101 includes one or more networks that facilitate communication between any number of components. The networks may include wired networks and/or wireless networks (e.g., and/or the Internet). The networks may operate in accordance with any number and types of communication protocols (e.g., such as the internet protocol).

In an embodiment, communication system 101 is implemented with one or more local communications links (e.g., a bus interconnecting a processor of imaging system 100 and any of the tiered storages).

While illustrated in FIG. 1 as including a limited number of specific components, a system in accordance with an embodiment may include fewer, additional, and/or different components than those illustrated therein.

Figure 2A:
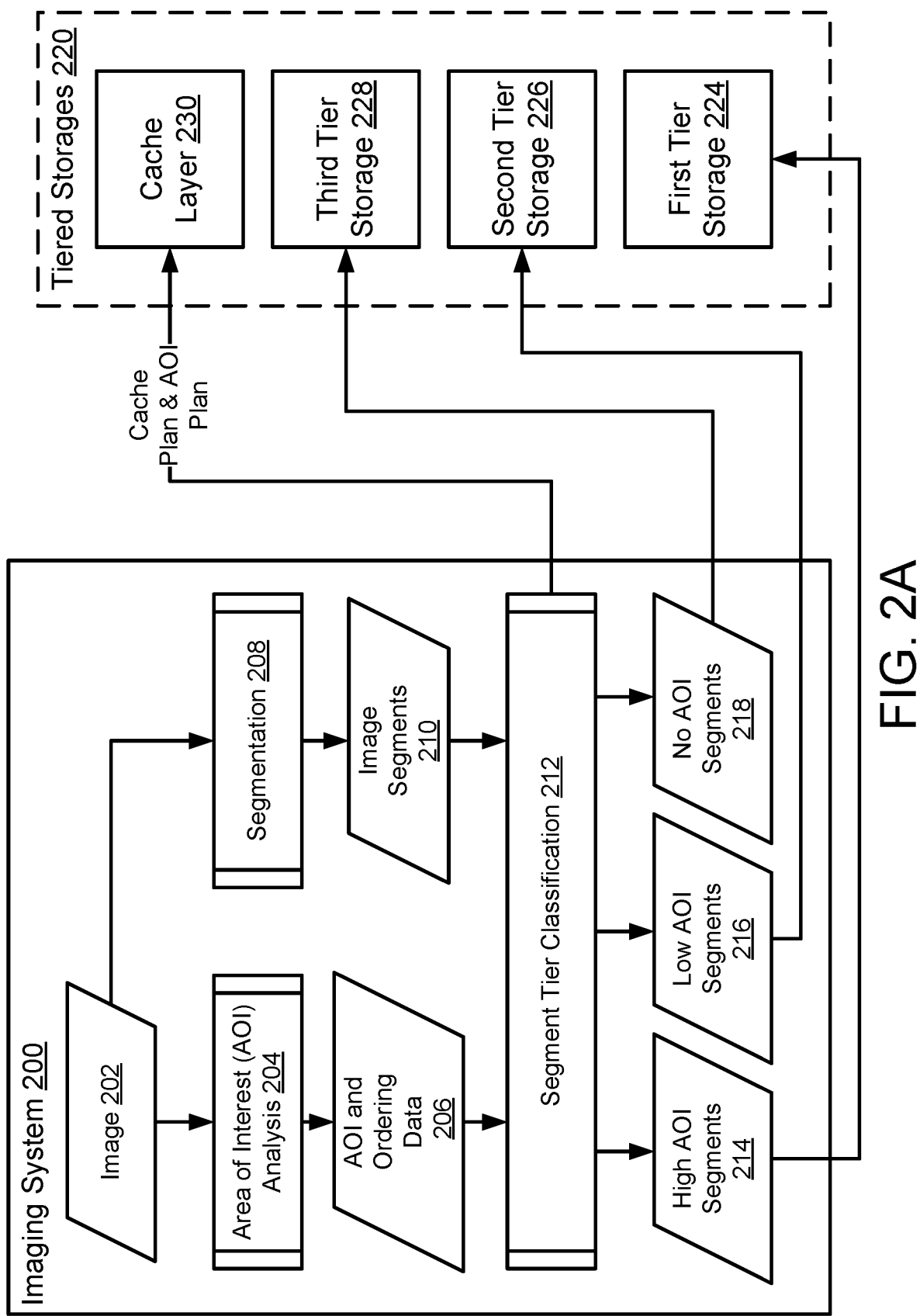
FIG. 2A shows a block diagram illustrating an imaging system and multiple tiered storages over time in accordance with an embodiment.

Turning to FIG. 2A, a data flow diagram in a system similar to that illustrated in FIG. 1 in accordance with an embodiment is shown. Imaging system 200 may be similar to imaging system 100, and tiered storages 220 may be similar to tiered storage 102.

Imaging system 200 may obtain image 202. Image 202 may be a data structure including information regarding a scene. For example, image 202 may be any type of image file. The image file may include lossy or lossless compression, may be of any family type (e.g., raster, vector, etc.) or a hybrid, and may include any quantity of information regarding a scene. The image file may be of any format (e.g., Joint Photographic Experts Group (JPEG), Tagged Image File Format (TIFF), Portable Network Graphics (PNG), Graphics Interchange Format (GIF), etc.). Image 202 may be obtained by receiving it from another device (e.g., an imaging device such as a camera), reading it from storage, or by generating it using an imaging device.

Imaging system 200 may perform an area of interest analysis 204 and/or segmentation 208 of image 202. These operations may generate data structures used to select storage location(s) for image 202, and/or store image 202.

Area of interest analysis 204 may identify one or more areas of interest 206 in image 202. Areas of interest 206 may correspond to regions (e.g., groups of pixels corresponding to portions of the depicted scene) of image 202. Each of the areas of interest may also be associated with a type reflecting a place within a hierarchy of the areas of interest (e.g., a primary area of interest, an auxiliary area of interest, etc.). In this manner, areas of interest of greater and/or lesser importance may be defined by the type of each of the areas of interest. The areas of interest may be identified by a SME in cooperation with imaging system 200 using, for example, a graphical user interface that allows the SME to view and provide user input that defines the areas of interests. The areas of interest may be identified via automated means such as with a trained neural network trained to identify and label areas of interest in images.

Segmentation 208 may segment image 202 into any number of image segments 210. Image 202 may be segmented using any method (e.g., dividing into a number of portions with approximately the same quantity of information for different portions of the depicted scene) without departing from embodiments disclosed herein. The boundaries of each of image segments 210 may or may not conform to the boundaries of area of interest 206.

Once obtained, image segments 210 may be subject to segment tier classification 212 processing based on areas of interest 206 corresponding to the image segments. Segment tier classification 212 may classify image segments 210 based on the corresponding areas of interest, and allocate the classified image segments for storage in different storage tiers based on the classification of each image segment.

For example, all image segments associated with areas of interest that are of a high level of importance may be classified as high area of interest segments 214. Similarly, all image segments associated with areas of interest that are of a low level of importance may be classified as low area of interest segments 216. In contrast, all image segments that are not associated with any areas of interest may be classified as no area of interest segments 218. These classifications may be used to perform lookups (or other processes) to identify storage tiers for storage of the corresponding image segments. Once identified, the image segments may be allocated for and stored in storages corresponding to the identified storage tiers.

As seen in FIG. 2A, all of the image segments classified as high area of interest segments 214 may be stored in first tier storage 224, which may be a high performance but costly storage (e.g., a solid state disk). The image segments classified as low area of interest segments 216 may be stored in second tier storage 226, which may be a moderate performance storage (e.g., a hard disk drive) and of moderate cost. In contrast, all of the image segments classified as no area of interest segments 218 may be stored in third tier storage 228, which may be a low performance but low cost storage (e.g., a tape drive).

By storing the image segments in this manner, the usability of the storage image may be improved while limiting cost for storing the image for subsequent use. For example, if access to the image is required in the future, the segments of the image corresponding to the portion of the scene most likely to be displayed may be stored in higher performance storage thereby facilitate rapid reading of the segments into memory to facilitate display of this portion of the scene on a display and/or subsequent use. In contrast, the image segments of the image corresponding to the portion of the scene that is unlikely to be displayed may be stored in lower performance but cost effective storage to reduce aggregate cost for storing image 202 for subsequent use.

In addition to classifying the segments, cache plans and area of interest plans may be generated through segment tier classification 212. The cache plan may specify a plan for caching image segments based on areas of interest. For example, the cache plan may specify relationships between the areas of interest, paths between areas of interest, supplementary areas (or procedures for establishing supplemental areas of interest), and/or other information which may be used to cache image segments as portions of an image are used by a user.

Like the cache plan, the area of interest plan may specify information regarding how to manage use of an image. The area of interest plan may provide information regarding recommendations for exploring the image. For example, the area of interest recommendation plan may indicate locations on images where graphical elements may be placed to direct a user's attention when viewing the image. The graphical element may indicate orderings between the areas of interest in which a user may explore the image.

Both plans may be generated based on ordering data for the areas of interest, which may be obtained through area of interest analysis 204. For example, the order in which the areas of interest are identified by a SME may be recorded and used to establish the cache plan and AOI plan. The plans may be based on other orderings (e.g., location based rather than based on the temporal order in which the areas of interest are obtained) of the areas of interest without departing from embodiments disclosed herein. While depicted in FIG. 2A as being stored in cache layer 230, copies of these plans may be stored in other locations (e.g., locally) without departing from embodiments disclosed herein.

Additionally, as noted above, multiple plan sets may be established based on the classifications of the areas of interest so that the plans may be filtered and implemented based on the roles of subsequent users.

Figure 2B:
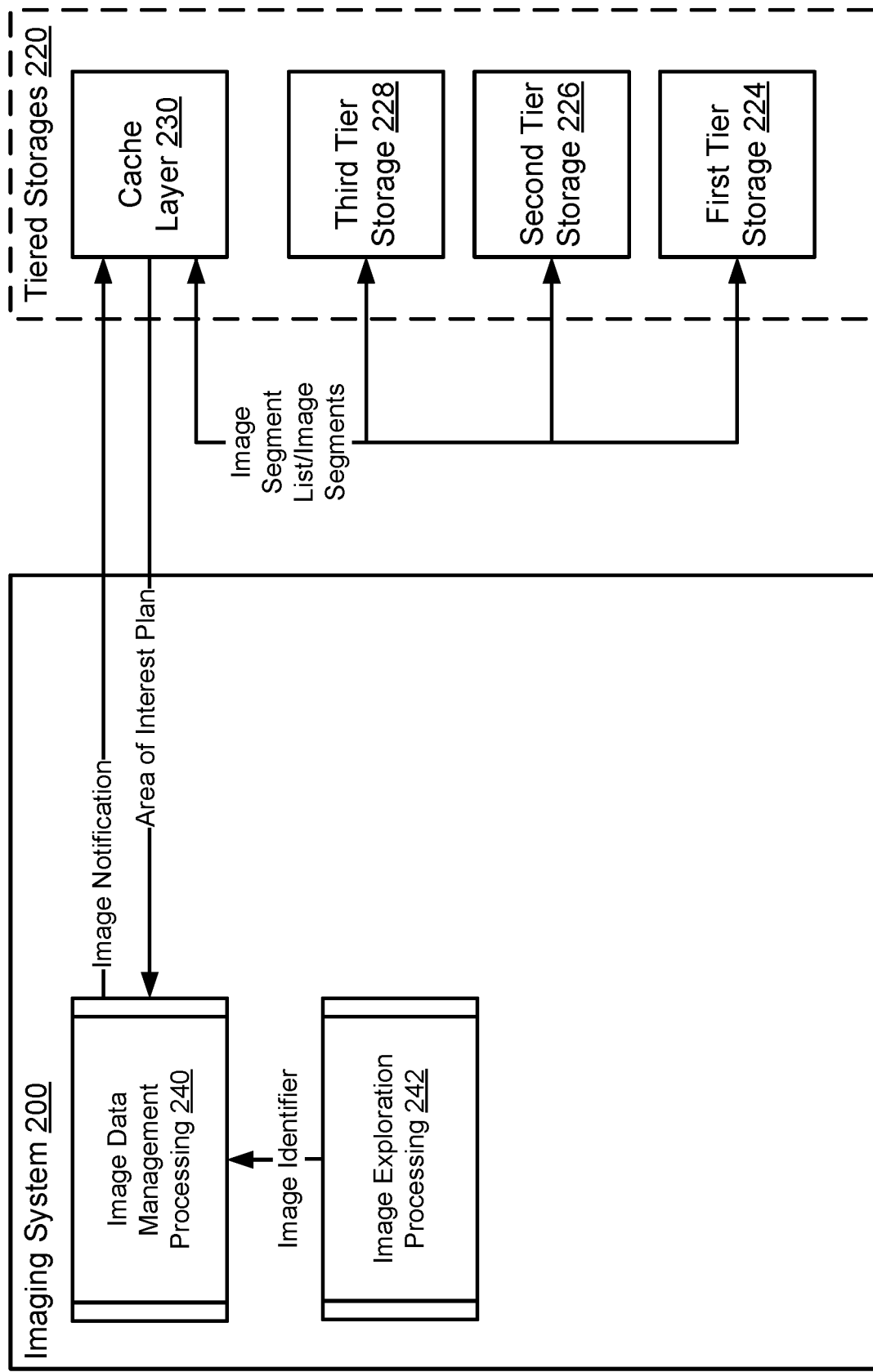
FIGS. 2B-D show block diagrams illustrating data flows in use of images in accordance with an embodiment.

Turning to FIG. 2B, a second data flow diagram in a system similar to that illustrated in FIG. 1 in accordance with an embodiment is shown. Once an image is stored, the image may be used through reading of the image from tiered storage 220. To improve read performance, when image exploration processing 242 (e.g., display of an image for a user that will explore the image) is initiated with respect to the image, image data management processing 240 may be automatically initiated. Image data management processing 240 may obtain an identifier of the image under processing and send an image notification to tiered storage 220 to initiate caching for the image.

Cache layer 230 may provide the area of interest plan for the identified image in response to the image notification. Additionally, the cache layer 230 may send out requests for lists of image segments to storages 224-228 to initially populate cache layer 230 with image segments corresponding to an initial view of the image. The image segments may be provided in response to the request to populate the cache layer.

Figure 2C:
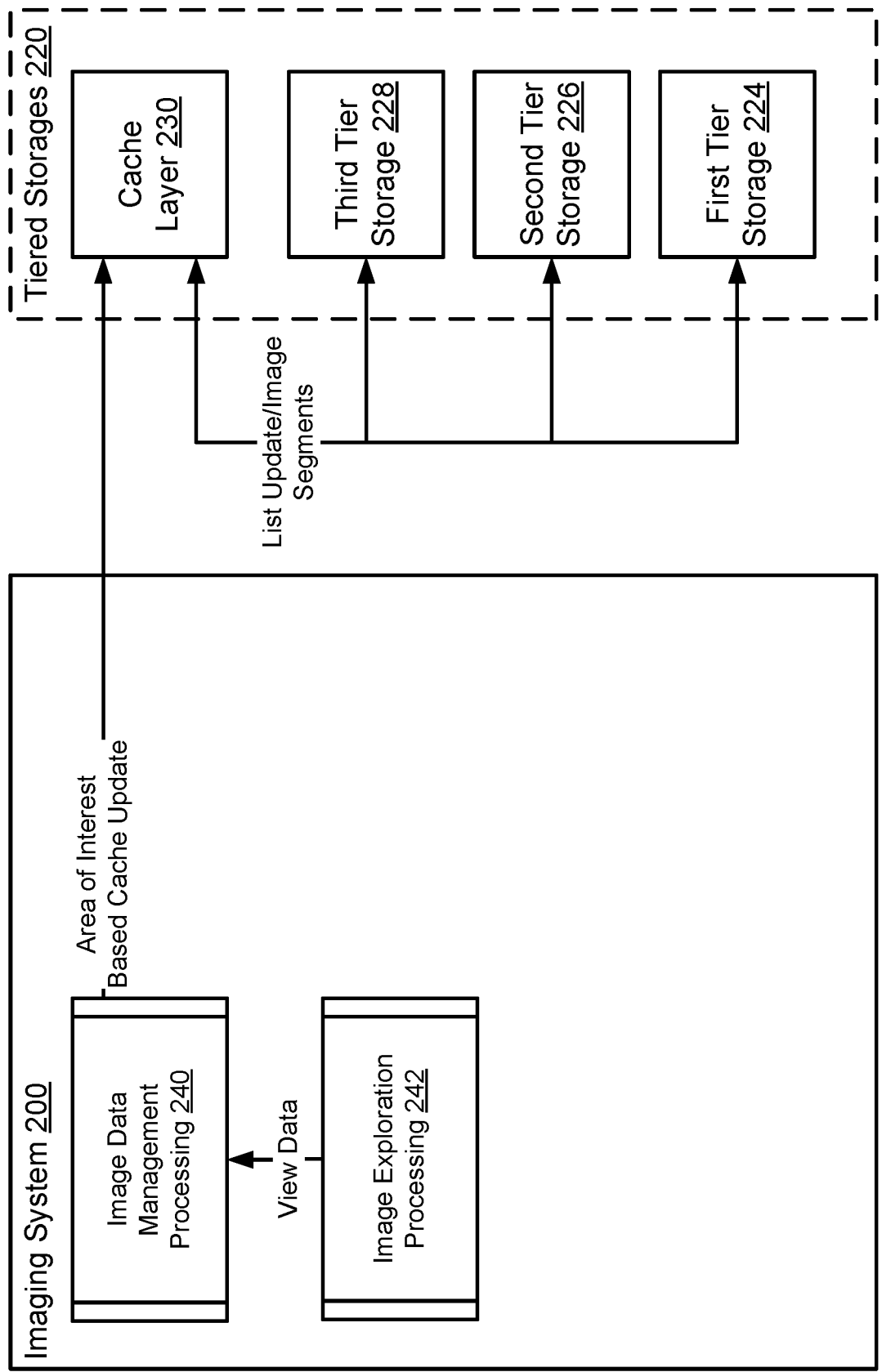

Turning to FIG. 2C, a third data flow diagram in a system similar to that illustrated in FIG. 1 in accordance with an embodiment is shown. As image exploration processing 242 begins to change the view of the image presented to a user based on user feedback, image data management processing 240 may track the view of the image to identify areas of interest in the view. Image data management processing 240 may use the identified areas of interest to identify, using the area of interest plan, other areas of interest, paths between the areas of interest, and/or supplemental areas associated with the viewed area of interest. Image data management processing 240 may send area of interest based cache updates based on these identified other areas of interest, paths between the areas of interest, and/or supplemental areas so that cache layer 230 may dynamically populate itself with image segments corresponding to these newly identified areas of interest.

Figure 2D:
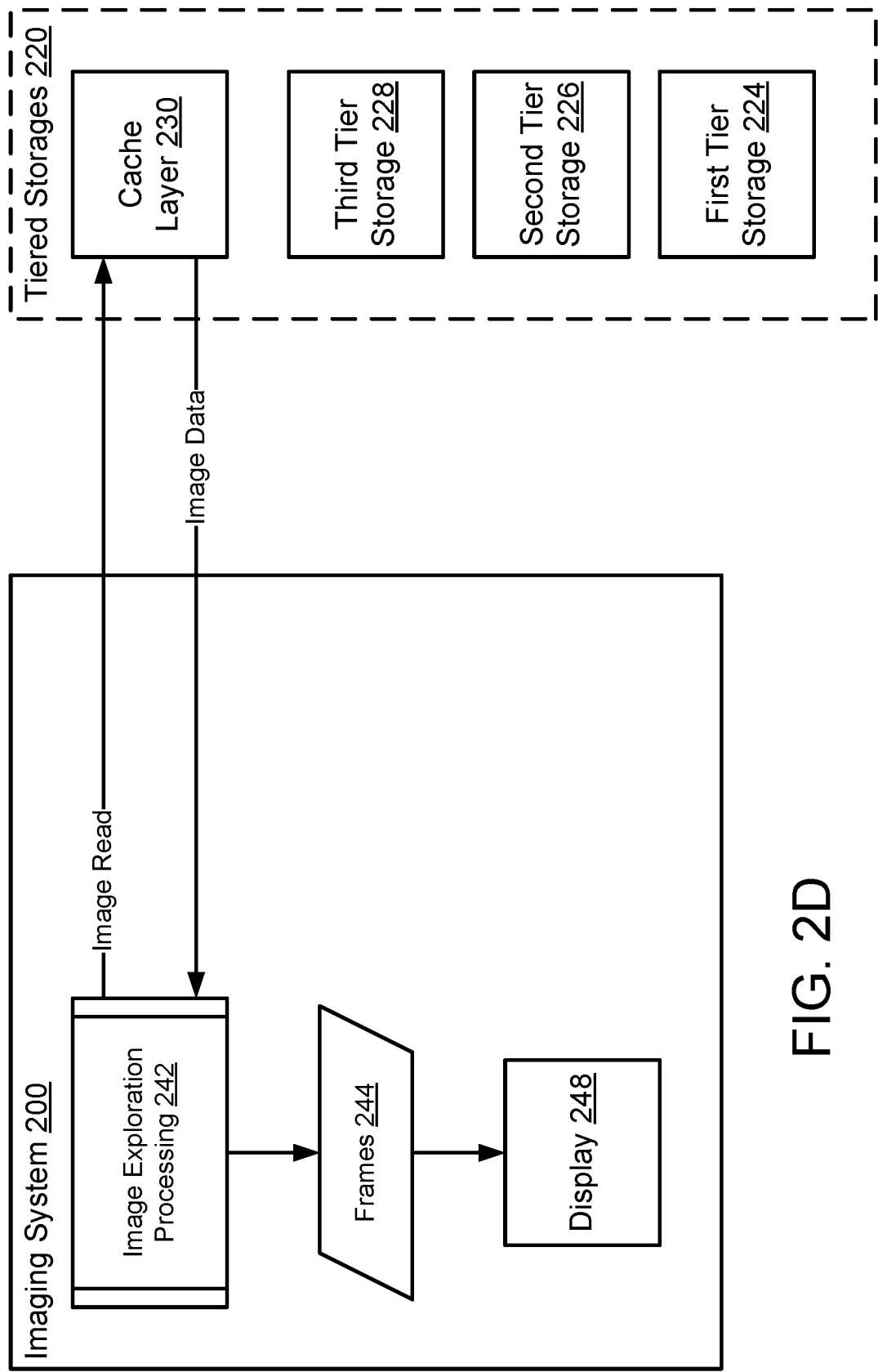

Turning to FIG. 2D, a fourth data flow diagram in a system similar to that illustrated in FIG. 1 in accordance with an embodiment is shown. As image exploration process 242 reads image segments from tiered storages 220 to provide view of the image as indicated by user input, the image data may be preferentially retrieved from cache layer 230 if available there. Otherwise, the image data may be read from one of the storages 224-228.

To improve the likelihood of the image segments from cache layer 230, image exploration processing 242 may generate views that include graphical elements that direct attention to areas of interest specified by the area of interest plan. For example, the graphical elements may include arrows or other graphical elements superimposed over portions of the image that indicate a direction that the user pan the image towards to observe relevant portions of the image. In an embodiment, the view and superimposed graphical elements may be displayed as part of a graphical user interface through which the user may provide user input. The user input may indicate, for example, selecting the super imposed graphical elements. If selected, a corresponding panning, zooming, or other image manipulation process may be automatically implemented to shift a view of the image to correspond to an area of interest associated with the graphical element. In this manner, the user may follow a predetermined viewing path through the image. The viewing path may correspond to the cached image segments so that most or all of the image segments are cached when needed to be read to generate view of the image along the viewing path.

The graphical elements and read image segments may be used to generate frames 244 with may correspond to graphical data for a frame in a graphical user interface presented to a user. The graphical user interface and frames 244 therein may be displayed to the user via display 248, which may be any number and type of hardware displays such as a computer monitor. For example, frames 244 may depict a view point with respect to an image. The view point may change over time. Frames 244 may be generated using any technique and may corresponding to any number of compiled still images presented over time to give the appearance of a moving picture.

Any of the processing as shown in FIGS. 2A-2D may be implemented with one or more processes executing on one or more data processing systems.

Figure 3A:
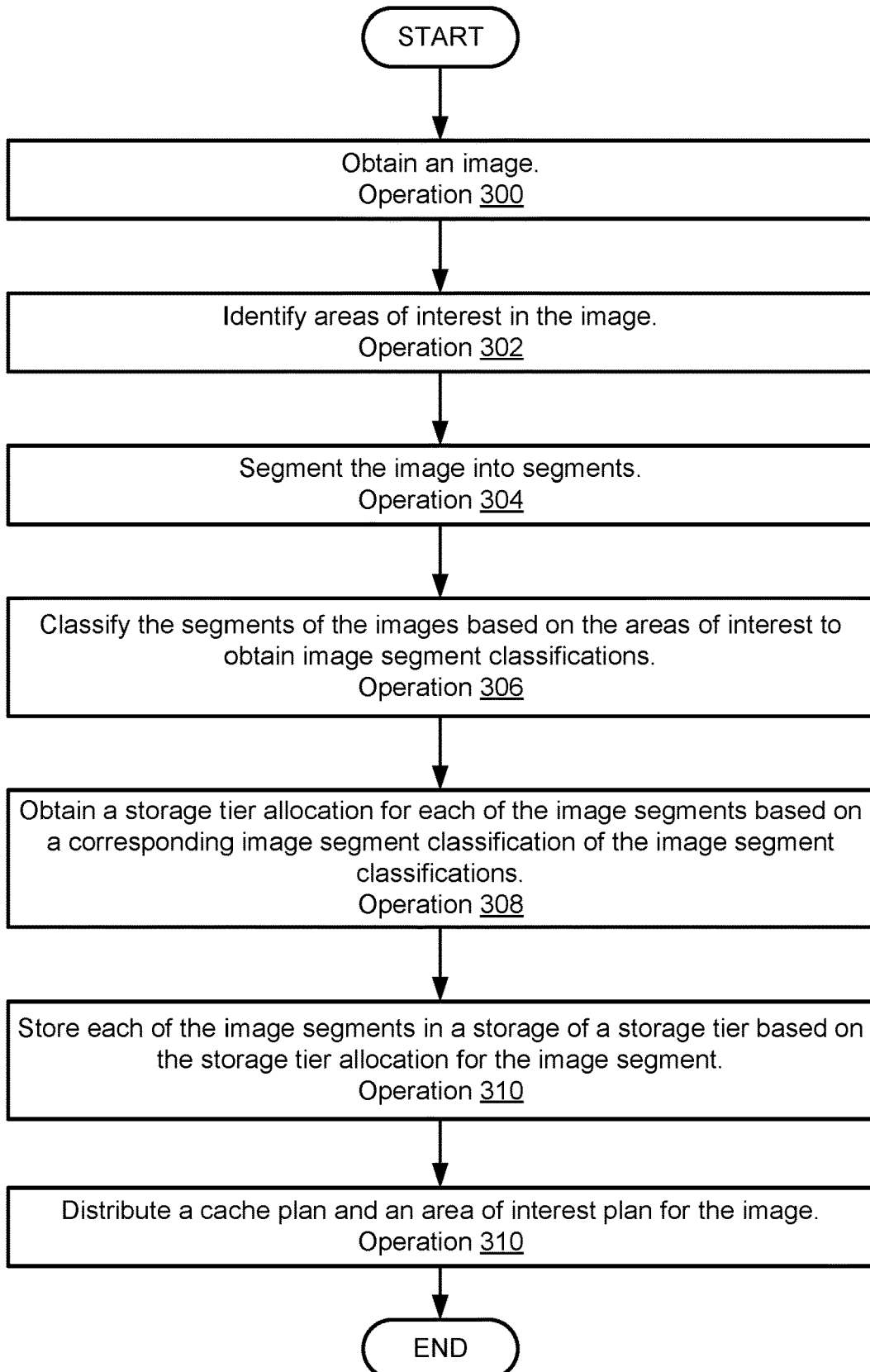
FIG. 3A shows a flow diagram illustrating a method of storing an image in accordance with an embodiment.
Figure 3B:
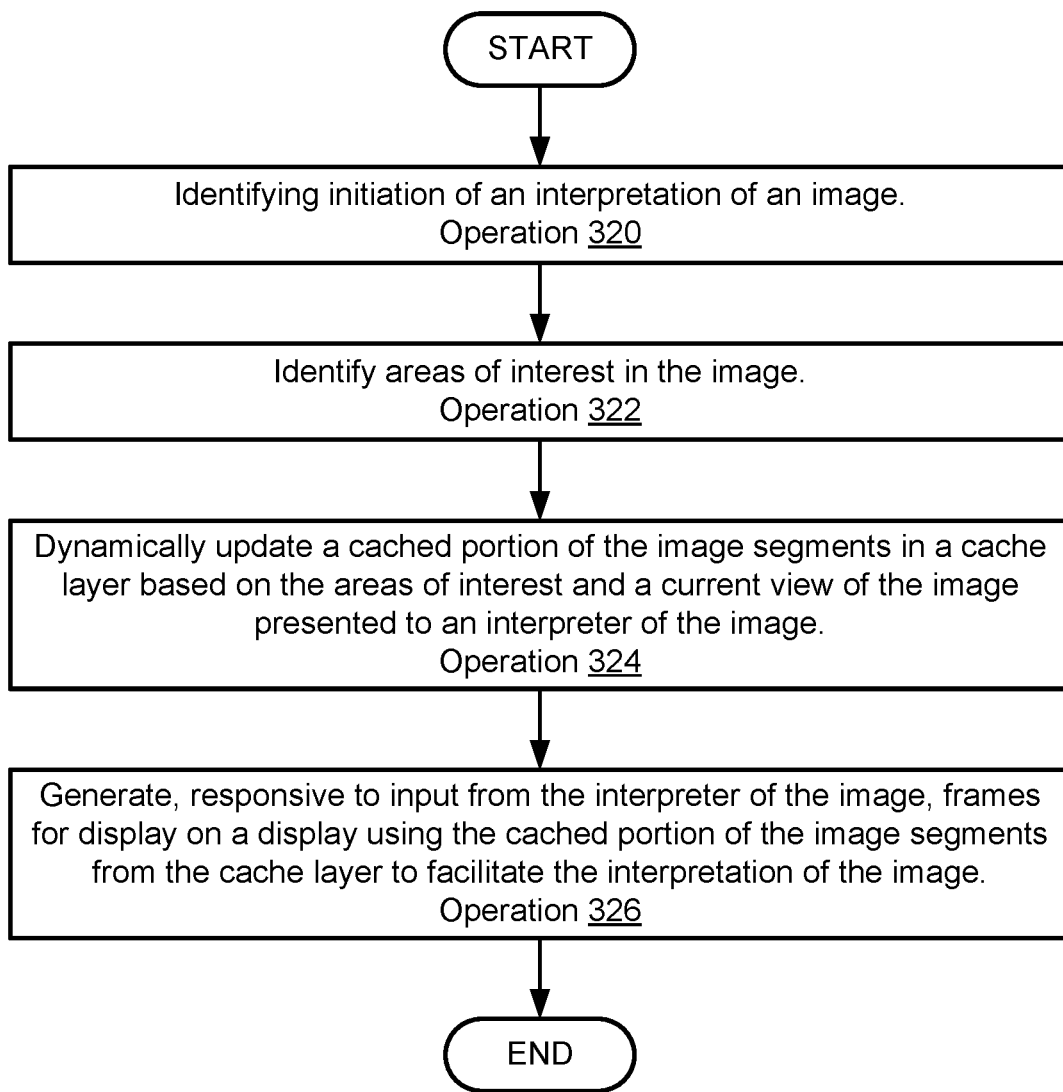
FIG. 3B shows a flow diagram illustrating a method of using an image in accordance with an embodiment.

As discussed above, the components of FIG. 1 may perform various methods to identify areas of interest in an image and use the areas of interest to manage downstream use of the image. FIGS. 3A-3B illustrate methods that may be performed by the components of FIG. 1. In the diagrams discussed below and shown in FIGS. 3A-3B, any of the operations may be repeated, performed in different orders, and/or performed in parallel with or in a partially overlapping in time manner with other operations.

Turning to FIG. 3A, a flow diagram illustrating a method of storing an image in accordance with an embodiment is shown. The method may be performed by an imaging system or another data processing system.

At operation 300, an image is obtained. The image may be obtained by (i) reading the image from storage, (ii) receiving the image from another device, and/or (iii) generating the image (e.g., capturing it) through use of an imaging device such as a camera.

The image may depict a scene. The image may be interpreted through, for example, automated analysis and/or cooperative analysis with a SME. The image may depict, for example, a group of cells and/or other human tissues, a manufacturing process, an accident scene, a construction site, and/or any other type of scene for which derived information based on the depicted scene may be desired for various purposes.

In an embodiment, the image is a super resolution image. For example, the image may include large amounts of information and may require gigabytes of storage space for storage.

At operation 302, areas of interest in the image are identified. The areas of interest may be identified (i) by reading them from storage (e.g., if they already exist) and/or (ii) through automated and/or cooperative analysis of the image with a SME. The automated analysis may be performed in cooperation with a SME through display of portions of the image to the SME, obtaining input from the SME through which areas of interest are designated. The activity of the SME may be monitored to, for example, identify an ordering with respect to areas of interest, identify paths between areas of interest, and/or identify supplemental areas. For example, any of these areas may be identified based on various areas of the image viewed by the SME. The order may correspond to the order in which the SME annotates the areas of interest.

The areas of interest may be part of a hierarchical system that defines some of the areas of interest as being higher or lower in the hierarchy. For example, areas of interest more critical to an outcome of a process through which the areas of interest are identified may be higher in the hierarchy while other areas of interest less critical to the outcome of the process may be lower in the hierarchy. Any number of areas of interest at any level within the hierarchy may be identified for the image.

At operation 304, the image is segmented into segments. The image segments may be portions of the image. The image segments may be similar or different amounts of the image.

At operation 306, the image segments are classified based on the areas of interest to obtain image segment classifications. The image segments may be classified based on their membership in the areas of interest. An image segment may be a member of an area of interest if the image segment includes of a portion of the image that lies within a boundary that defines the area of interest. The memberships in the areas of interest may be used to calculate a value representative of a likelihood of the image segment being accessed in the future. The value may be used to classify the image segment into one of any number of groups (e.g., primary areas of interest, auxiliary areas of interest, etc.) of image segments. The aforementioned process may be repeated for each image segment to classify each of the image segments.

Additionally, cache plans and area of interest plans for the image may be obtained. These plans, as noted above, may be based on area of interest ordering, paths between the areas of interest, and/or supplemental areas. The plans may be stored locally and/or in storage (remote and/or local).

At operation 308, a storage tier allocation for each of the image segments is obtained. The storage tier allocation for each of the image segments may be based on a corresponding image segment classification for the respective image segment. For example, a lookup (or other process) may be performed based on the corresponding image segment classification to identify the storage tier allocation for each image segment. The storage tier allocation may, for example, indicate where an image segment is stored, provide a plan for managing storage of the image segment (e.g., levels of redundancy, migration plans, etc.), a resolution or other information regarding the fidelity of the image segment, and/or may provide other information regarding storage of the image segment. A storage tier allocation for each segment may be obtained.

At operation 310, each of the image segments is stored in a storage of a storage tier based on the corresponding storage tier allocation. The image segments may be stored by providing the image segments to the respective storages and/or instructions to store the image segments in the corresponding storages. The copies of the image segments provided to the storage may be performed to the fidelity levels and/or other information specified in the storage allocation.

For example, the storage tier allocation for image segments that are not associated with areas of interest may indicate that these image segments are to be stored in a reduced resolution format (or at a prescribed level of fidelity). In this manner, both the cost for the storage tier and the quantity of resources of the storage tier used to store an image segment may be scaled based on the relative importance of each image segment.

Additionally, in some embodiments, the storage tier allocation for the image segments may specify a level of redundancy such that, depending on the image segment classifications: (i) lowest fidelity copies of image segments may be stored in archival storage tiers, (ii) lower fidelity copies of the image segments may be stored in lower tiered storage, and/or (iii) full or high fidelity copies of the image segments may be stored in higher tiered storage.

The method may end following operation 310.

Using the method illustrated in FIG. 3A, images may be stored in a cost efficient manner across different storage tiers. To prepare for desirable behavior on read, the cache and area of interest plans may be used to dynamically cache some of these image segments to higher performance cache storage.

Turning to FIG. 3B, a flow diagram illustrating a method of managing use of an image in accordance with an embodiment is shown. The method may be performed by an imaging system or another data processing system.

At operation 320, initiation of an interpretation of an image is identified. The initiation may be identified by receiving a notification indicating that interpretation of the image is beginning. For example, an application tasked with generation a graphical user interface through which the image may be interpreted may send a notification when the interpretation begins.

At operation 322, areas of interest in the image are identified. The areas of interest may be identified by reading the area of interest plan and/or cache plan for the image. These data structures may include the aforementioned information and/or other information usable to manage use of the image. These plans may be identified, for example, by filtering these plans from a repository of plans that are keyed to roles or other characteristics of users. The filtering may be performed on the basis, for example, of a role of the interpreter of the image so that the implemented plans are based on the areas of interest added by previous interpreters performing similar roles.

At operation 324, a cached portion of image segments for the image is dynamically updated based on the areas of interest in the image and a current view of the image as presented to an interpreter of the image. For example, as the current view of the image is updated (e.g., based on user input), the areas of interest (e.g., changed area of interest) in the view may be identified. The areas of interest in the view may be used in conjunction with relationships between the areas of interest, paths between the areas of interest, and supplemental areas corresponding to the areas of interest to identify portions of image segments to be added to a cache layer. Thus, as the area of interest in the view changes, different portions of image segments corresponding to the associated areas of interests, paths, and supplemental areas may be added to the cache so that if the view moves to these associated areas the corresponding image segments may be efficiently read from the cache layer. Refer to FIGS. 4A-4E for additional details regarding relationships between areas of interest, paths, and supplemental areas.

At operation 326, frames for display on a display are generated using the cached portion of the image segments. The frames maybe generated responsive to input from the interpreter of the image. For example, when a view of the image is initially centered on a first area of interest, image segments corresponding to a path from the first area of interest to a second area of interest may be cached. If a user then provides user input that pans along this path, the view of the image may be correspondingly updated, and frames for these views along the path may be generated using the pre-cached image segments corresponding to the path, which may extend a significant distance from the first area of interest and the local area in which the view was originally centered. The frames may be generated using any frame compilation process.

The frames may also include graphical elements such as, for example, arrows based on an area of interest plan. The areas may be superimposed over or otherwise integrated with portions of the image to direct attention of the user towards other areas of interest in a particular order that corresponds to the cache plan. Thus, if the user elects to follow the graphical elements, image segments may be pre-cached to provide an enhanced experience. For example, the system may appear highly responsive by virtue of the pre-cached image segments. In contrast, reading the image segments from storage rather than cache may take significantly longer thereby reducing the performance level of the system as perceived by the user.

The method may end following operation 326.

Using the method illustrated in FIGS. 3A-3B, embodiments disclosed herein may provide a system that identifies areas of interest in images and uses these area of interest to guide subsequent use of the images. By doing so, the perceived performance of the system may be improved through, for example, image segment caching based on viewed areas of interest, and relationships between areas of interest, paths, and supplemental areas.

Turning to FIGS. 4A-4E, diagrams illustrating a process of using an image in accordance with an embodiment are shown.

Figure 4A:
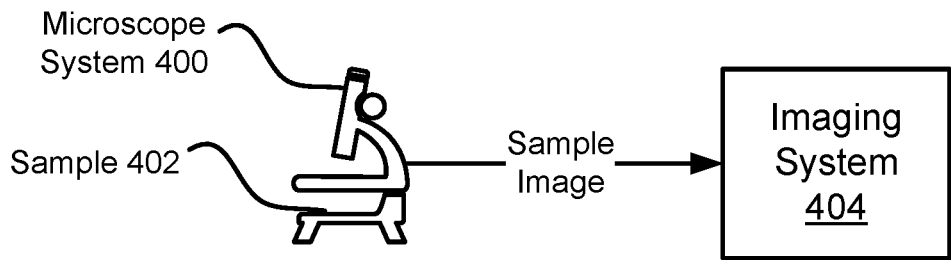
FIGS. 4A-4E show diagrams illustrating a system, operations performed thereby, and data structures used by the system over time in accordance with an embodiment.

Turning to FIG. 4A, consider a scenario in which a medical image of sample 402 useful for medical diagnosis purposes is obtained using microscope system 400, which may include a camera and some number of lenses used to project a depiction of sample 402 on a capture device of the camera. The sample image may be obtained by imaging system 404, which may be similar to the imaging system illustrated in FIG. 1.

Figure 4B:
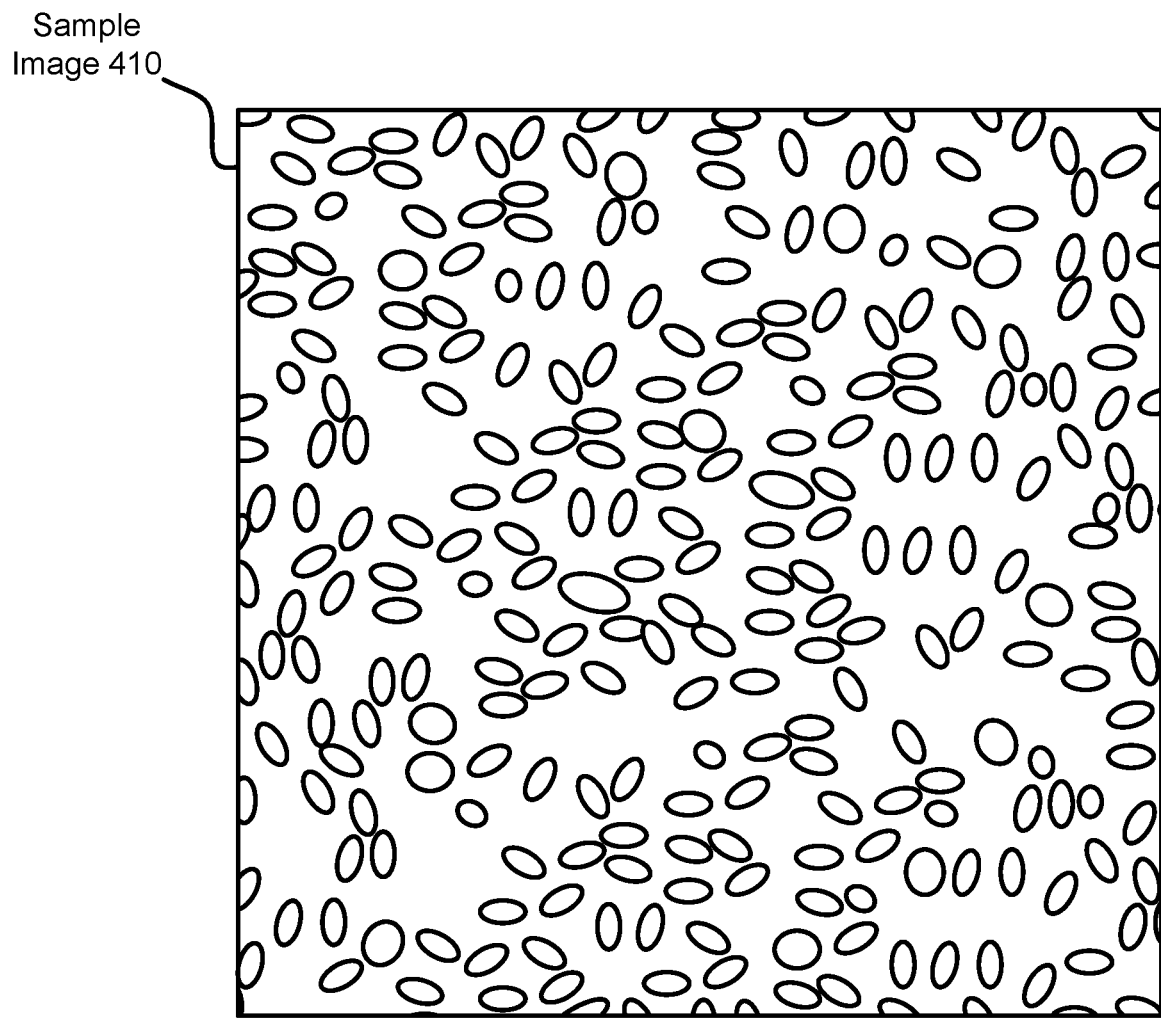

Turning to FIG. 4B, a diagram of sample image 410 in accordance with an embodiment is shown. Sample image 410 may be complex and include many features regarding a scene. For example, sample 402 may be a tissue sample from a person. In FIG. 4B, the circles within the border of sample image 410 may represent portions of the image corresponding to cells, proteins, and/or other portions of the tissue. To perform a medical diagnosis, the content and structure of these cells, proteins, and/or other portions of the tissue may be analyzed (e.g., by a SME). As part of that analysis, an outcome (e.g., a medical diagnosis in this example) and one or more areas of interest for the image may be identified.

Figure 4C:
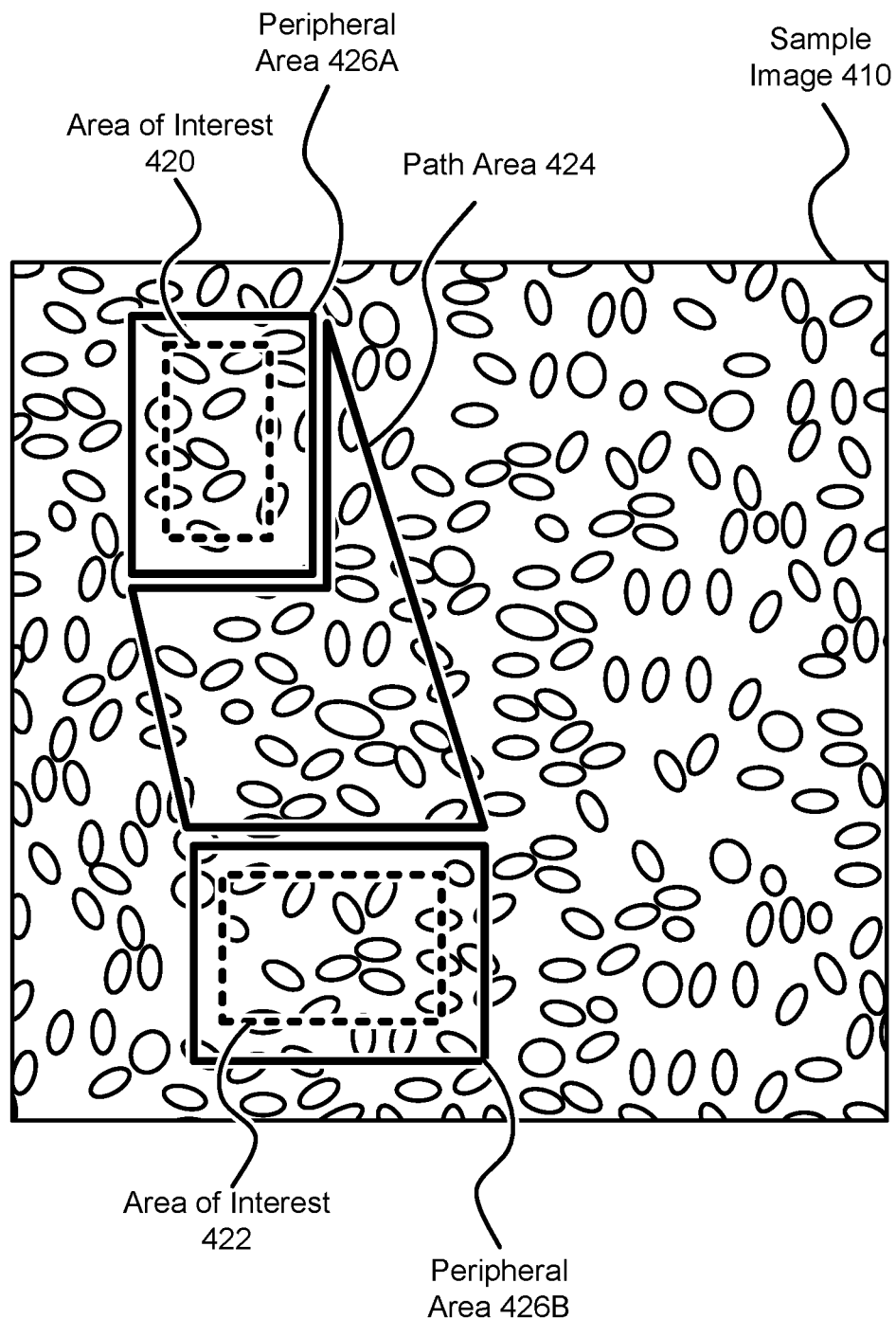

Turning to FIG. 4C, a second diagram of sample image 410 in accordance with an embodiment is shown and includes annotations reflecting two areas of interest 422. As noted above, the analysis process for sample image 410 may include a cooperative process performed with a SME. The SME may explore and add annotations to sample image 410 as part of the analysis. To do so, portions of sample image 410 may be presented to the SME via a graphical user interface.

In this example, the SME identified area of interest 420 (which may correspond to a first diagnostically relevant landmark) and area of interest 422 (which may correspond to a second diagnostically relevant landmark). While only these two areas of interest were identified, the SME may have explored a majority of sample image 410, which may be a time consuming process.

To manage subsequent use of the image, as noted above, the image may be segmented and various plans may be established. For example, to guide subsequent interpretation of the image an area of interest plan may be developed that indicates ordering in which the areas of interest should be reviewed to confirm the medical diagnosis. This order may correspond to the order in which the SME identified the areas of interest 420, 422.

The plans may also include a cache plan. As noted above, a cache plan may identify associated portions of sample image 410 when another portion is being viewed or otherwise used. The cache plan may correspond to the area of interest plan so that as the area of interest plan is followed, image segments are cached ahead of viewings of the areas of interest in the order specified by the area of interest plan.

To do so, cache plans may be keyed to areas of interest and identify other areas of the image that should be cached when the keyed area of interest is viewed or otherwise used. These other areas may include, for example: (i) other areas of interest, (ii) paths between the area of interest and the other areas of interest, and (iii) supplemental areas.

The other areas of interest may correspond to the same ordering of areas of interest in the area of interest plan. For example, if an area of interest plan specifies that area of interest 420 is to be viewed first and area of interest 422 is to be viewed second, then the cache plan may indicate that area of interest 422 is to be cached when area of interest 420 is viewed or otherwise in use (e.g., being read/has been read).

The paths between the areas of interest may correspond to the portion of the image between two areas of interest. For example, path area 424 may represent the path between area of interest 420 and area of interest 422 supplemented with peripheral areas 426A, 426B (discussed below).

The supplemental areas may include a buffer area around the area(s) of interest and/or paths to, for example, reduce the likelihood of an aggressive pan, an aggressive exploration, or other image manipulation resulting in a read for the image that is serviced with image segments that are not cached. For example, peripheral areas 424A, 424B may include an area around the periphery of the areas of interest of sufficient size that risk of such reads is reduced. The peripheral areas may be established using a formula, may be dynamically selected based on behavior of the user (e.g., the rate at which a user pans or overshoots areas that the user subsequent reviews), and/or may be established via other methods.

Using the cache plan for area of interest 420, for example, the image segments corresponding to peripheral area 424A, path area 424, peripheral area 426B, and area of interest 422 may be automatically cached when area of interest 420 is viewed or otherwise used (e.g., read).

Figure 4D:
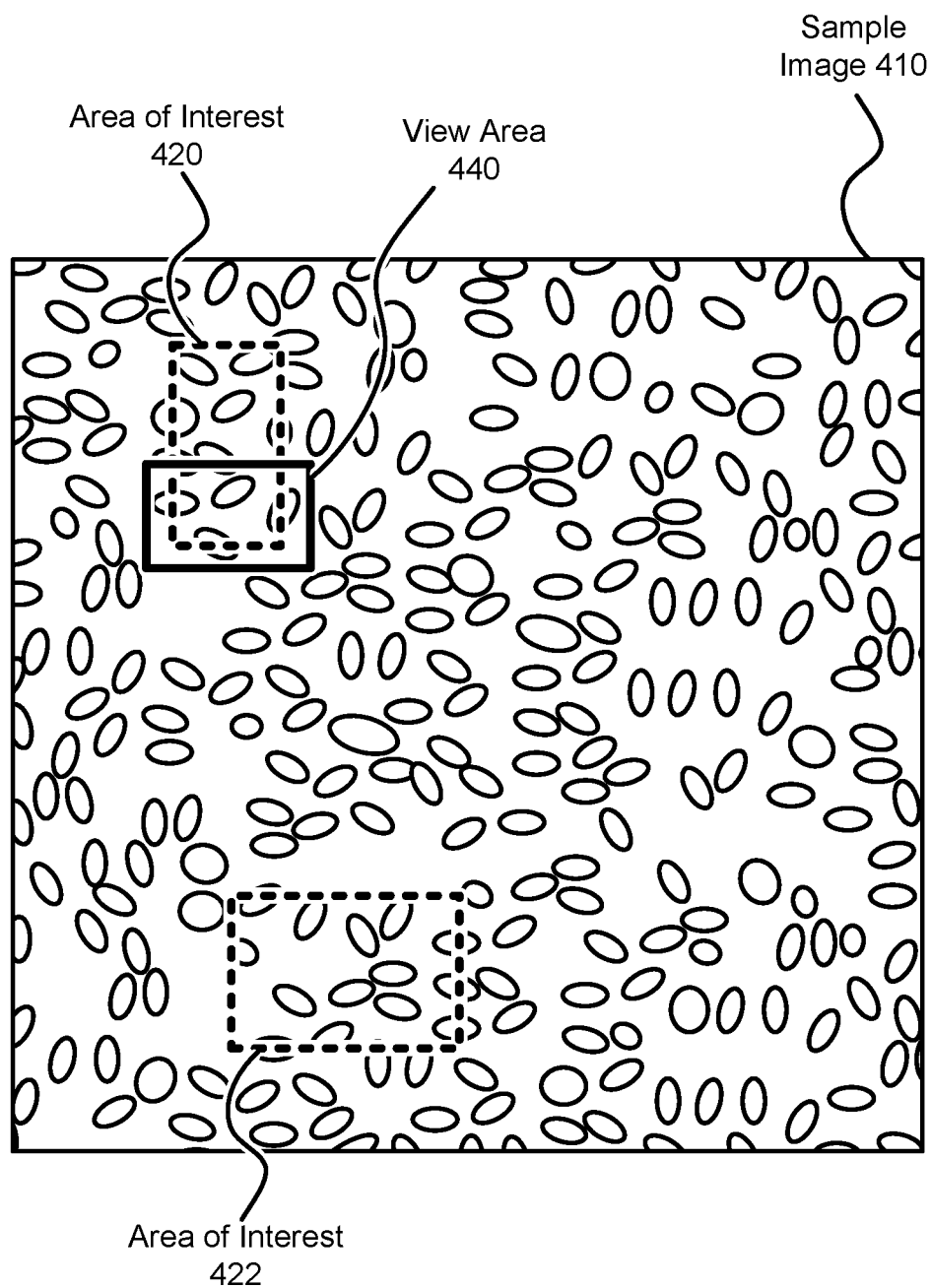

Once these plans are established and image segments stored, use of the image may be serviced more efficiently. Turning to FIG. 4D, a third diagram of sample image 410 in accordance with an embodiment is shown. Now consider a scenario where a user begins to use sample image 410 by viewing the portion of sample image 410 corresponding to view area 440. To present this view, frames may begin to be generated and displayed to the user, which may initiate the dynamic cache updating as described with respect to FIG. 2B.

Figure 4E:
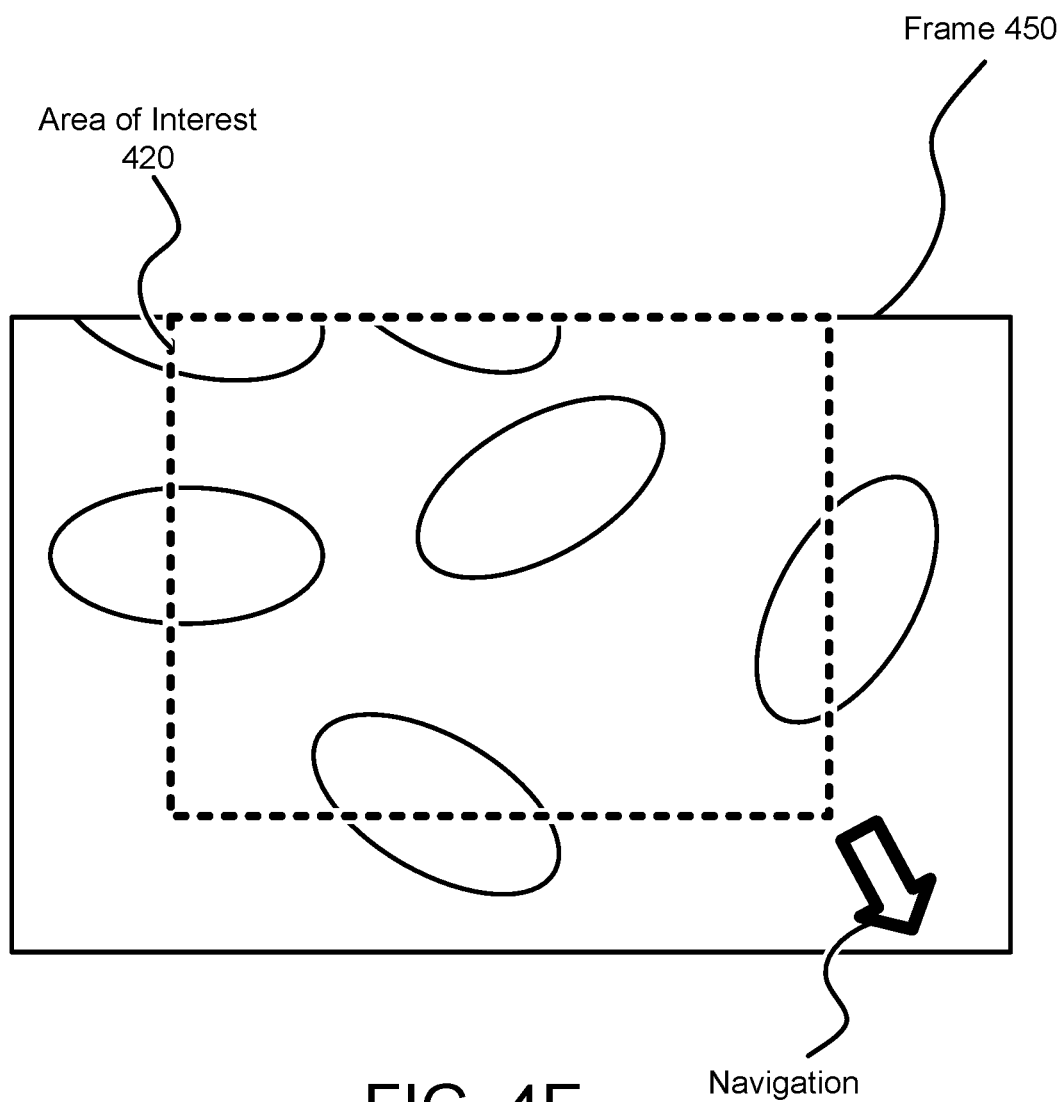

Turning to FIG. 4E, a diagram of frame 450 in accordance with an embodiment is shown. Frame 450 may be a graphical element positioned in a frame of a graphical user interface. As seen in FIG. 4E, frame 450 may represent the viewed area, and may be constructed using image segments corresponding to this area. Once displayed, a user may begin to explore the image.

To assist the user to explore sample image 410 in an efficient manner, navigation tool 452 may be present in frame 450. Navigation tool 452 may be a graphical element added to frame 450 that conveys, to the user, a suggested order in which areas of interest should be viewed. For example, navigation tool 452 may be implemented with an arrow (and/or other graphical depictions) indicating that the user should pan the image to reach a next area of interest as specified in an area of interest plan and for which the dynamically updated cache has cached image segments (and also, for example, image segments for the path to the next area of interest and corresponding supplemental areas). While shown in FIG. 4E with respect to an arrow, a graphical elements for navigation may include additional elements such as, for example, text, symbols, or other types of elements indicating (i) a relationship between the associated areas of interest, (ii) information regarding regard the area of interest such as landmarks included therein or comments from a previous interpreter added to the area of interest, and/or (iii) other information regarding the areas of interest.

Navigation tool 452 may be a passive (e.g., an annotation) or active (e.g., interactive) element. If interactive, a user may position a pointer with navigation tool 452 and provide user input to indicate selection of navigation tool 452. When selected, navigation tool 452 may automatically pan, zoom, and/or otherwise manipulate the view of sample image 410 presented to follow the path to the next area of interest.

By doing so, embodiments disclosed herein may improve the use of images by (i) managing storage cost and performance through use of cost efficient storage in combination with caching, (ii) reduce duration of subsequent use by providing additional information regarding previous use of an image, and/or (iii) automate subsequent interpretation processes to prevent undesired reads of image segments that are not cached.

Figure 5:
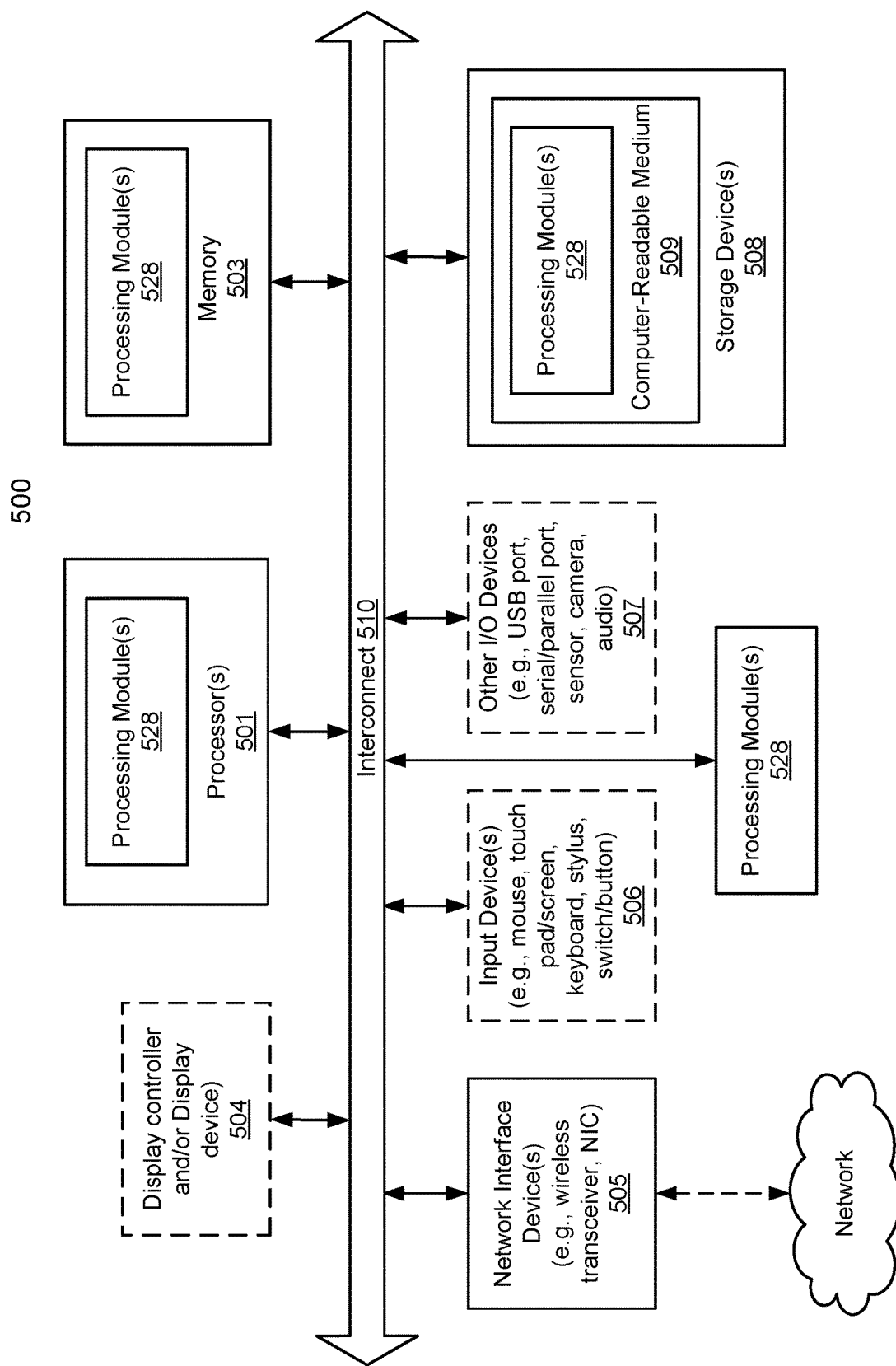
FIG. 5 shows a block diagram illustrating a data processing system in accordance with an embodiment.

Any of the components illustrated in FIGS. 1-4E may be implemented with one or more computing devices. Turning to FIG. 5, a block diagram illustrating an example of a data processing system (e.g., a computing device) in accordance with an embodiment is shown. For example, system 500 may represent any of data processing systems described above performing any of the processes or methods described above. System 500 can include many different components. These components can be implemented as integrated circuits (ICs), portions thereof, discrete electronic devices, or other modules adapted to a circuit board such as a motherboard or add-in card of the computer system, or as components otherwise incorporated within a chassis of the computer system. Note also that system 500 is intended to show a high level view of many components of the computer system. However, it is to be understood that additional components may be present in certain implementations and furthermore, different arrangement of the components shown may occur in other implementations. System 500 may represent a desktop, a laptop, a tablet, a server, a mobile phone, a media player, a personal digital assistant (PDA), a personal communicator, a gaming device, a network router or hub, a wireless access point (AP) or repeater, a set-top box, or a combination thereof. Further, while only a single machine or system is illustrated, the term "machine" or "system" shall also be taken to include any collection of machines or systems that individually or jointly execute a set (or multiple sets) of instructions to perform any one or more of the methodologies discussed herein.

In one embodiment, system 500 includes processor 501, memory 503, and devices 505-507 via a bus or an interconnect 510. Processor 501 may represent a single processor or multiple processors with a single processor core or multiple processor cores included therein. Processor 501 may represent one or more general-purpose processors such as a microprocessor, a central processing unit (CPU), or the like. More particularly, processor 501 may be a complex instruction set computing (CISC) microprocessor, reduced instruction set computing (RISC) microprocessor, very long instruction word (VLIW) microprocessor, or processor implementing other instruction sets, or processors implementing a combination of instruction sets. Processor 501 may also be one or more special-purpose processors such as an application specific integrated circuit (ASIC), a cellular or baseband processor, a field programmable gate array (FPGA), a digital signal processor (DSP), a network processor, a graphics processor, a network processor, a communications processor, a cryptographic processor, a co-processor, an embedded processor, or any other type of logic capable of processing instructions.

Processor 501, which may be a low power multi-core processor socket such as an ultra-low voltage processor, may act as a main processing unit and central hub for communication with the various components of the system. Such processor can be implemented as a system on chip (SoC). Processor 501 is configured to execute instructions for performing the operations discussed herein. System 500 may further include a graphics interface that communicates with optional graphics subsystem 504, which may include a display controller, a graphics processor, and/or a display device.

Processor 501 may communicate with memory 503, which in one embodiment can be implemented via multiple memory devices to provide for a given amount of system memory. Memory 503 may include one or more volatile storage (or memory) devices such as random access memory (RAM), dynamic RAM (DRAM), synchronous DRAM (SDRAM), static RAM (SRAM), or other types of storage devices. Memory 503 may store information including sequences of instructions that are executed by processor 501, or any other device. For example, executable code and/or data of a variety of operating systems, device drivers, firmware (e.g., input output basic system or BIOS), and/or applications can be loaded in memory 503 and executed by processor 501. An operating system can be any kind of operating systems, such as, for example, Windows® operating system from Microsoft®, Mac OS®/iOS® from Apple, Android® from Google®, Linux®, Unix®, or other real-time or embedded operating systems such as VxWorks.

System 500 may further include IO devices such as devices (e.g., 505, 506, 507, 508) including network interface device(s) 505, optional input device(s) 506, and other optional IO device(s) 507. Network interface device(s) 505 may include a wireless transceiver and/or a network interface card (NIC). The wireless transceiver may be a WiFi transceiver, an infrared transceiver, a Bluetooth transceiver, a WiMax transceiver, a wireless cellular telephony transceiver, a satellite transceiver (e.g., a global positioning system (GPS) transceiver), or other radio frequency (RF) transceivers, or a combination thereof. The NIC may be an Ethernet card.

Input device(s) 506 may include a mouse, a touch pad, a touch sensitive screen (which may be integrated with a display device of optional graphics subsystem 504), a pointer device such as a stylus, and/or a keyboard (e.g., physical keyboard or a virtual keyboard displayed as part of a touch sensitive screen). For example, input device(s) 506 may include a touch screen controller coupled to a touch screen. The touch screen and touch screen controller can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with the touch screen.

IO devices 507 may include an audio device. An audio device may include a speaker and/or a microphone to facilitate voice-enabled functions, such as voice recognition, voice replication, digital recording, and/or telephony functions. Other IO devices 507 may further include universal serial bus (USB) port(s), parallel port(s), serial port(s), a printer, a network interface, a bus bridge (e.g., a PCI-PCI bridge), sensor(s) (e.g., a motion sensor such as an accelerometer, gyroscope, a magnetometer, a light sensor, compass, a proximity sensor, etc.), or a combination thereof. IO device(s) 507 may further include an imaging processing subsystem (e.g., a camera), which may include an optical sensor, such as a charged coupled device (CCD) or a complementary metal-oxide semiconductor (CMOS) optical sensor, utilized to facilitate camera functions, such as recording photographs and video clips. Certain sensors may be coupled to interconnect 510 via a sensor hub (not shown), while other devices such as a keyboard or thermal sensor may be controlled by an embedded controller (not shown), dependent upon the specific configuration or design of system 500.

To provide for persistent storage of information such as data, applications, one or more operating systems and so forth, a mass storage (not shown) may also couple to processor 501. In various embodiments, to enable a thinner and lighter system design as well as to improve system responsiveness, this mass storage may be implemented via a solid state device (SSD). However, in other embodiments, the mass storage may primarily be implemented using a hard disk drive (HDD) with a smaller amount of SSD storage to act as a SSD cache to enable non-volatile storage of context state and other such information during power down events so that a fast power up can occur on re-initiation of system activities. Also a flash device may be coupled to processor 501, e.g., via a serial peripheral interface (SPI). This flash device may provide for non-volatile storage of system software, including a basic input/output software (BIOS) as well as other firmware of the system.

Storage device 508 may include computer-readable storage medium 509 (also known as a machine-readable storage medium or a computer-readable medium) on which is stored one or more sets of instructions or software (e.g., processing module, unit, and/or processing module/unit/logic 528) embodying any one or more of the methodologies or functions described herein. Processing module/unit/logic 528 may represent any of the components described above. Processing module/unit/logic 528 may also reside, completely or at least partially, within memory 503 and/or within processor 501 during execution thereof by system 500, memory 503 and processor 501 also constituting machine-accessible storage media. Processing module/unit/logic 528 may further be transmitted or received over a network via network interface device(s) 505.

Computer-readable storage medium 509 may also be used to store some software functionalities described above persistently. While computer-readable storage medium 509 is shown in an exemplary embodiment to be a single medium, the term "computer-readable storage medium" should be taken to include a single medium or multiple media (e.g., a centralized or distributed database, and/or associated caches and servers) that store the one or more sets of instructions. The terms "computer-readable storage medium" shall also be taken to include any medium that is capable of storing or encoding a set of instructions for execution by the machine and that cause the machine to perform any one or more of the methodologies of embodiments disclosed herein. The term "computer-readable storage medium" shall accordingly be taken to include, but not be limited to, solid-state memories, and optical and magnetic media, or any other non-transitory machine-readable medium.

Processing module/unit/logic 528, components and other features described herein can be implemented as discrete hardware components or integrated in the functionality of hardware components such as ASICS, FPGAs, DSPs or similar devices. In addition, processing module/unit/logic 528 can be implemented as firmware or functional circuitry within hardware devices. Further, processing module/unit/logic 528 can be implemented in any combination hardware devices and software components.

Note that while system 500 is illustrated with various components of a data processing system, it is not intended to represent any particular architecture or manner of interconnecting the components; as such details are not germane to embodiments disclosed herein. It will also be appreciated that network computers, handheld computers, mobile phones, servers, and/or other data processing systems which have fewer components or perhaps more components may also be used with embodiments disclosed herein.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments disclosed herein also relate to an apparatus for performing the operations herein. Such a computer program is stored in a non-transitory computer readable medium. A non-transitory machine-readable medium includes any mechanism for storing information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices).

The processes or methods depicted in the preceding figures may be performed by processing logic that comprises hardware (e.g. circuitry, dedicated logic, etc.), software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Embodiments disclosed herein are not described with reference to any particular programming language. It will be appreciated that a variety of programming languages may be used to implement the teachings of embodiments disclosed herein.

In the foregoing specification, embodiments have been described with reference to specific exemplary embodiments thereof. It will be evident that various modifications may be made thereto without departing from the broader spirit and scope of the embodiments disclosed herein as set forth in the following claims. The specification and drawings are, accordingly, to be regarded in an illustrative sense rather than a restrictive sense.

What is claimed is:

1. A method for managing exploration of an image that is segmented into image segments which are stored across tiers of a tiered storage, the method comprising:
   identifying initiation of an interpretation of the image;
   identifying areas of interest in the image;
   during the interpretation of the image:
      dynamically updating a portion of the image segments that is stored as cached data in a cache layer of a tiered storage to add parts to or remove parts from the portion stored as cached data from the cache layer based on:
         the areas of interest, and
         a current view of the image presented to an interpreter of the image; and
      generating, responsive to input from the interpreter of the image, frames for display on a display using the portion of the image segments that is stored as cached data in the cache layer to facilitate the interpretation of the image.

2. The method of claim 1, wherein dynamically updating the portion of the image segments that is stored as the cached data in the cache layer comprises:
   identifying a first area of interest of the areas of interest that is depicted in the current view;
   identifying a second area of interest of the areas of interest based on a previous interpretation of the image, the second area of interest not being in the current view including the first area of interest but is associated with the first area of interest; and
   adding, to the portion of the image segments that is stored as the cached data in the cache layer, a portion of the image segments of the image that correspond to the second area of interest.

3. The method of claim 2, wherein dynamically updating the portion of the image segments that is stored as the cached data in the cache layer further comprises:
   adding, to the portion of the image segments that is stored as the cached data in the cache layer, a second portion of the image segments of the image that correspond to a path between the first area of interest and the second area of interest, the path excluding any part of the first area of interest and the second area of interest and excluding other ones of the areas of interest within the image segments.

4. The method of claim 3, wherein dynamically updating the portion of the image segments that is stored as the cached data in the cache layer further comprises:
   adding, to the portion of the image segments that is stored as the cached data in the cache layer, a third portion of the image segments of the image that correspond to a periphery around the first area of interest, the periphery excluding any part of other ones of the areas of interest within the image segments.

5. The method of claim 1, wherein the areas of interest correspond to portions of the image annotated during a previous interpretation of the image.

6. The method of claim 5, wherein the areas of interest are associated with one another based on distances between pairs of the areas of interest.

7. The method of claim 1, wherein generating, responsive to the input from the interpreter of the image, the frames comprises:
for a frame of the frame:
adding a representation of a navigation tool to the frame, the navigation tool guiding a user viewing the frame on the display from a first area of interest of the areas of interest to a second area of interest of the areas of interest, the navigation tool further conveying a suggested order for viewing the first area of interest and the second area of interest.

8. The method of claim 7, wherein generating, responsive to the input from the interpreter of the image, the frames further comprises:
for the frame of the frame:
using a portion of the portion of the image segments that is stored as the cached data in the cache layer to generate a representation of the image for the current view.

9. A non-transitory machine-readable medium having instructions stored therein, which when executed by a processor, cause the processor to perform operations for managing exploration of an image that is segmented into image segments which are stored across tiers of a tiered storage, the operations comprising:
identifying initiation of an interpretation of the image;
identifying areas of interest in the image;
during the interpretation of the image:
dynamically updating a portion of the image segments that is stored as cached data in a cache layer of a tiered storage to add parts to or remove parts from the portion stored as cached data from the cache layer based on:
the areas of interest, and
a current view of the image presented to an interpreter of the image; and
generating, responsive to input from the interpreter of the image, frames for display on a display using the portion of the image segments that is stored as cached data the cache layer to facilitate the interpretation of the image.

10. The non-transitory machine-readable medium of claim 9, wherein dynamically updating the portion of the image segments that is stored as the cached data in the cache layer comprises:
identifying a first area of interest of the areas of interest that is depicted in the current view;
identifying a second area of interest of the areas of interest based on a previous interpretation of the image, the second area of interest not being in the current view including the first area of interest but is associated with the first area of interest; and
adding, to the portion of the image segments that is stored as the cached data in the cache layer, a portion of the image segments of the image that correspond to the second area of interest.

11. The non-transitory machine-readable medium of claim 10, wherein dynamically updating the portion of the image segments that is stored as the cached data in the cache layer further comprises:
adding, to the portion of the image segments that is stored as the cached data in the cache layer, a second portion of the image segments of the image that correspond to a path between the first area of interest and the second area of interest.

12. The non-transitory machine-readable medium of claim 11, wherein dynamically updating the portion of the image segments that is stored as the cached data in the cache layer further comprises:
adding, to the portion of the imager segments that is stored as the cached data in the cache layer, a third portion of the image segments of the image that correspond to a periphery around the first area of interest.

13. The non-transitory machine-readable medium of claim 9, wherein the areas of interest correspond to portions of the image annotated during a previous interpretation of the image.

14. The non-transitory machine-readable medium of claim 13, wherein the areas of interest are associated with one another based on distances between pairs of the areas of interest.

15. A data processing system, comprising:
a processor; and
a memory coupled to the processor to store instructions, which when executed by the processor, cause the processor to perform operations for managing exploration of an image that is segmented into image segments which are stored across tiers of a tiered storage, the operations comprising:
identifying initiation of an interpretation of the image;
identifying areas of interest in the image;
during the interpretation of the image:
dynamically updating a portion of the image segments that is stored as cached data in a cache layer of a tiered storage to add parts to or remove parts from the portion stored as cached data from the cache layer based on:
the areas of interest, and
a current view of the image presented to an interpreter of the image; and
generating, responsive to input from the interpreter of the image, frames for display on a display using the portion of the image segments that is stored as cached data in the cache layer to facilitate the interpretation of the image.

16. The data processing system of claim 15, wherein dynamically updating the portion of the image segments that is stored as the cached data in the cache layer comprises:
identifying a first area of interest of the areas of interest that is depicted in the current view;
identifying a second area of interest of the areas of interest based on a previous interpretation of the image, the second area of interest not being in the current view including the first area of interest but is associated with the first area of interest; and
adding, to the portion of the image segments that is stored as the cached data in the cache layer, a portion of the image segments of the image that correspond to the second area of interest.

17. The data processing system of claim 16, wherein dynamically updating the portion of the image segments that is stored as the cached data in the cache layer further comprises:
adding, to the portion of the image segments that is stored as the cached data in the cache layer, a second portion of the image segments of the image that correspond to a path between the first area of interest and the second area of interest.

18. The data processing system of claim 17, wherein dynamically updating the portion of the image segments that is stored as the cached data in the cache further comprises:

adding, to the portion of the image segments that is stored as the cached data in the cache layer, a third portion of the image segments of the image that correspond to a periphery around first area of interest.

19. The data processing system of claim 15, wherein the areas of interest correspond to portions of the image annotated during a previous interpretation of the image.

20. The method of claim 1, wherein the interpreter is a live person that is reviewing the image in real time.

* * * * *